US010385160B2

(12) United States Patent
Weippert

(10) Patent No.: US 10,385,160 B2
(45) Date of Patent: *Aug. 20, 2019

(54) AMINE-CATALYZED THIOL-CURING OF EPOXY RESINS

(71) Applicant: TOOZ TECHNOLOGIES GMBH, Aalen (DE)

(72) Inventor: Hans-Joachim Weippert, Aalen (DE)

(73) Assignee: TOOZ TECHNOLOGIES GMBH, Aalen (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/935,965

(22) Filed: Mar. 26, 2018

(65) Prior Publication Data

US 2018/0215864 A1    Aug. 2, 2018

Related U.S. Application Data

(63) Continuation of application No. 15/118,339, filed as application No. PCT/EP2015/052948 on Feb. 12, 2015, now Pat. No. 10,179,831.

(30) Foreign Application Priority Data

Feb. 13, 2014  (DE) ................ 10 2014 202 609

(51) Int. Cl.

| C08F 2/46 | (2006.01) |
| C08F 2/50 | (2006.01) |
| C08G 61/04 | (2006.01) |
| C08G 59/66 | (2006.01) |
| C08G 59/50 | (2006.01) |
| C08K 5/3445 | (2006.01) |
| C08K 5/3462 | (2006.01) |
| C08K 5/37 | (2006.01) |
| C08G 59/40 | (2006.01) |
| C08G 59/68 | (2006.01) |
| C08G 59/22 | (2006.01) |
| C08G 59/24 | (2006.01) |
| C09J 163/00 | (2006.01) |
| G01N 1/36 | (2006.01) |
| F21V 8/00 | (2006.01) |
| G02B 27/01 | (2006.01) |
| C08K 5/54 | (2006.01) |

(52) U.S. Cl.
CPC .......... *C08G 59/66* (2013.01); *C08G 59/226* (2013.01); *C08G 59/245* (2013.01); *C08G 59/4021* (2013.01); *C08G 59/5053* (2013.01); *C08G 59/686* (2013.01); *C08K 5/3445* (2013.01); *C08K 5/3462* (2013.01); *C08K 5/37* (2013.01); *C09J 163/00* (2013.01); *G01N 1/36* (2013.01); *G02B 6/0001* (2013.01); *G02B 27/0172* (2013.01); *C08K 5/54* (2013.01); *G01N 2001/364* (2013.01); *G02B 2027/0178* (2013.01)

(58) Field of Classification Search
CPC .... C08G 59/66; C08G 59/245; C08G 59/226; C08G 59/686; G01N 1/36; G01N 2001/364; G02B 2027/0178; G02B 27/0172; G02B 6/001; C09J 163/00

USPC .......... 522/42, 33, 6, 71, 189, 184, 1; 520/1
See application file for complete search history.

(56) References Cited

U.S. PATENT DOCUMENTS

| 3,873,502 | A | 3/1975 | Hicknet et al. |
| 3,914,288 | A | 10/1975 | Garnish et al. |
| 4,177,173 | A | 12/1979 | Carr |
| 4,927,902 | A * | 5/1990 | Johnson ................ C07C 323/25 525/504 |
| 4,990,679 | A | 2/1991 | Wolf et al. |
| 5,143,999 | A | 9/1992 | Setiabudi et al. |
| 5,413,999 | A | 5/1995 | Vacca et al. |
| 5,608,115 | A * | 3/1997 | Okazaki ................ C07C 321/14 568/61 |
| 6,100,362 | A | 8/2000 | Okazaki et al. |
| 6,100,632 | A | 8/2000 | Okazaki et al. |
| 7,781,484 | B2 | 8/2010 | Byers et al. |
| 7,884,289 | B2 | 2/2011 | Weekamp et al. |
| 8,676,571 | B2 | 3/2014 | Otani et al. |
| 8,703,844 | B2 | 4/2014 | Burckhardt et al. |
| 2002/0176046 | A1* | 11/2002 | Kitamura ............... C08G 59/66 349/153 |
| 2005/0197390 | A1 | 9/2005 | Byers et al. |
| 2005/0249891 | A1 | 11/2005 | Kitamura et al. |
| 2006/0111520 | A1* | 5/2006 | Byers ................ C08G 18/3876 525/452 |
| 2007/0112100 | A1 | 5/2007 | Byers et al. |
| 2009/0270554 | A1 | 10/2009 | Gilmore et al. |
| 2010/0105794 | A1 | 4/2010 | Dietliker et al. |
| 2010/0184899 | A1 | 7/2010 | Rao et al. |
| 2011/0130479 | A1 | 6/2011 | Kramer et al. |
| 2013/0261228 | A1 | 10/2013 | Marks |
| 2015/0047059 | A1 | 2/2015 | Chibuya et al. |
| 2017/0174823 | A1* | 6/2017 | Weippert ............... C08G 59/66 |

FOREIGN PATENT DOCUMENTS

| CN | 1388818 A | 1/2003 |
| EP | 0 014 745 A1 | 9/1980 |

(Continued)

OTHER PUBLICATIONS

Blickenstorfer et al, Photolatent Base Catalysts for Adhesives, RadTech report, Jul./Aug. 2010, pp. 10-16 (Year: 2010).*

(Continued)

*Primary Examiner* — Jessica Whiteley
(74) *Attorney, Agent, or Firm* — Patterson Thuente Pedersen, P.A.

(57) ABSTRACT

A composition containing an epoxide compound with two or more epoxide groups, a thiol ester with two or more ester groups and two or more thiol groups and/or a thiol ether with two or more thiol groups, and 0.005-2 wt. %, based on the total weight of the composition, of a tertiary amine which has a 5- or 6-membered aliphatic nitrogen heterocycle, said composition containing less than 1 wt. % of a primary amine. The composition can be used as an embedding medium for microscopy and as an adhesive and to an optical element which comprises the composition.

18 Claims, 3 Drawing Sheets

(56) References Cited

FOREIGN PATENT DOCUMENTS

| | | |
|---|---|---|
| EP | 0 014 745 B1 | 9/1980 |
| EP | 0 370 446 A2 | 5/1990 |
| EP | 0 665 219 A1 | 8/1995 |
| EP | 2 145 908 A1 | 1/2010 |
| EP | 2 145 908 B1 | 1/2010 |
| EP | 2 336 213 A1 | 6/2011 |
| EP | 2 336 213 B1 | 6/2011 |
| GB | 1 292 214 A | 10/1972 |
| JP | 7-109365 | 4/1995 |
| JP | 2007-526939 | 9/2007 |
| JP | 2008-63189 | 3/2008 |
| JP | 2008-268846 | 11/2008 |
| JP | 2009-504887 | 2/2009 |
| JP | 2009-126974 | 6/2009 |
| JP | 2009-173744 * | 8/2009 |
| JP | 2009-173744 A | 8/2009 |
| JP | 2011027027 A | 2/2011 |
| JP | 2011-519388 | 7/2011 |
| JP | 2013-545868 | 12/2013 |
| JP | 2014-001291 | 1/2014 |
| JP | 2015/048402 | 3/2015 |
| WO | WO 2008/119688 A1 | 10/2008 |

OTHER PUBLICATIONS

BASF The Chemical Company, Product Specification CGI 90, Product Specification: PS-212876, Analytical Method: KBC-212876; Version 3 effective from: Jun. 11, 2013, 1 page.
Ciba Specialty Chemicals: Coating Effects Segment Technology Center BL Coatings; Confidential Information—Covered by Secrecy Agreement; Formulation and Handling Guidelines CGI 90, created on Sep. 1, 2008; 4 pages.
H. Lucke et al., "Flexibel, bestandig und dicht", ADHASION 38-7-8/94, pp. 18-21 (in German).
S. Witzel, "Synthese neuer funktioneller Polysulfid-Telechele und deren industrielle Applikation", Dissertation Zuk Erlangung des akademischen Grades doctor rerum naturalium (Dr. rer. Nat.) Friedrich-Schiller-Universitat, Jena Mar. 14, 2007, 161 pages (in German).
International Preliminary Report on Patentability for corresponding International Application No. PCT/EP2015/052948 dated Aug. 16, 2016; 5 pages.
International Search Report for corresponding International Application No. PCT/EP2015/052948 dated Apr. 16, 2015; 3 pages; English translation 2 pages; 5 pages total.
Written Opinion of the International Search Authority for corresponding International Application No. PCT/EP2015/052948 dated Apr. 16, 2015; 4 pages; English translation 3 pages; 7 pages total.
BASF The Chemical Company, Product Specification CHI 90, Product Specification: PS-212876, Analytical Method: KBC-212876; Version 3 effective from: Jun. 11, 2013, 1 page.
Ciba Specialty Chemicals: Coating Effects Segment Technology Center BI Coatings; Confidential Information—Covered by Secrecy Agreement; Formulation and Handling Guidelines CGI 90, created on Sep. 1, 2008; 4 pages.
Ciba European Coatings Show; Benno Blickenstorfer, "Making Things Better with Ciba: New Opportunities in Adhesives using photolatent case technology", European Coatings Show, 2009, 26 pages.
H. Lucke et al., "Flexibel, bestandig und dieht", ADHASION 37-7-8/94, pp. 18-21 (in German).
S. Witzel, "Synthese neuer funktioneller Polysulfid-Telechele und deren industrielle Applikation", Dissertation Zue Erlangung des akademischen Grades doctor rerum naturalium (Dr. rer. Nat.) Friedrich-Schiller-Universitat, Jena Mar. 14, 2007, 161 pages (in German).
Benno Blickenstorfer et al., Ciba Inc., Switzerland: "New Opportunities in Adhesives using Photolatent Bases Technology". 8 pages.
XP-002738216 (Database WPI/Thomson, Week 200953, Thomson Scientific, London, AN 2009-M21250, 4 pages.

* cited by examiner

AMINE-CATALYZED THIOL-CURING OF EPOXY RESINS

RELATED APPLICATIONS

The present application is a continuation of U.S. patent application Ser. No. 15/118,339, filed on Aug. 11, 2016, a National Phase entry of PCT Application No. PCT/EP2015/052948, filed Feb. 12, 2015, which claims priority from DE Patent Application No. 102014202609.1, filed Feb. 13, 2014, said applications being hereby incorporated by reference herein in their entirety.

FIELD OF THE INVENTION

The present invention relates to a composition based on epoxy resins and thiols which can be polymerized using an amine catalyst and to the use thereof as an embedding medium for microscopy, as an adhesive and as a cement as well as to an optical element which contains the composition.

BACKGROUND OF THE INVENTION

For adhesives, in particular structural adhesives which are used in precision mechanics and optics, there is an increasing need for short curing times. Reaction adhesives with short curing times usually also have short processing times. However, from a technical point of view sufficiently long processing times are often required, for example in order to align precisely the work pieces to be bonded. Polyurethane adhesives and amine-cured epoxy resins are known as commercially available adhesives which cure at room temperature. With a processing time of approx. one hour, the curing time at room temperature to achieve the final strength is in the range of around one to two days.

A reduction in the curing time can be achieved by using light-curing adhesives, provided that the adherend surfaces are sufficiently translucent and there are no shadow zones. In the case of large adhesive surfaces it is necessary to realize a homogeneous illumination level so that the adhesive can cure uniformly and with low stress. In addition, hybrid systems or dual-curing adhesives are known as alternatives which, in addition to UV curing can also cure in a darkness curing through humidity or through heat. The investigations on commercially available dual-curing structural adhesives carried out within the framework of the present invention have shown, however, that the polymer formed by darkness curing differs significantly from the polymer formed by UV polymerization. Without exception, the usage properties of investigated cured adhesives were not satisfactory. Furthermore, the conditions required for a dark reaction are unfavourable for bonding precision mechanical and optical devices since the humidity in cleanrooms often falls below the required humidity of at least 50% relative humidity and, in addition, optic housings are often flushed with nitrogen for drying.

For thermal post-curing reactions, temperatures of 80° C. and above are often required, which can lead to stresses or sometimes to damage to components. In the case of anaerobic darkness curing, the problem arises that the materials suitable for this are often not present in precision mechanical optical devices and special primers must be applied as activators before the adhesive process.

In the case of commercially available rapid-curing adhesives based on epoxides, despite processing times of often only a few minutes, the final strengths are only achieved after approx. 5-20 hours (in the case of curing at room temperature). In the case of such short processing times, there is also the problem that the wetting of the adhesive surfaces rapidly becomes insufficient, whereby the bonding strength deteriorates significantly, in particular after exposure to damp heat.

For the microscopic investigation of samples, for example tissue sections, it is usual to embed the samples in a transparent medium. The embedding medium creates the optical conditions for the microscopic investigation, protects the sample from mechanical damage and serves to preserve the sample in the long term. For high image quality, the optical properties of the embedding medium are of decisive importance, in particular a refractive index and dispersion which can be adapted to the microscopy technique used and the type of preparation to be investigated as well as a high transmittance and low residual fluorescence of the embedding medium. The refractive index of the embedding medium is to be able to be adapted as closely as possible to the refractive index of the glass of the specimen slide used and cover glass or, in the case of immersion microscopy, to the refractive index of the immersion medium, in order to achieve as low a spherical aberration as possible. In the case of such embedding media, a short curing time accompanied by a sufficiently long processing time, curing at room temperature to protect the biological samples to be embedded and good adhesion to the embedded samples are also desirable. In the case of specific preparations, however, it can also be necessary for the (cured) embedding medium to have as high a refractive index as possible, whereby high imaging qualities are then produced during microscopic examination.

Furthermore, in the case of specific optical applications, it can be necessary for the refractive power in the cured state of an adhesive used to be adapted to the refractive power of the optical components used. Adhesives for optical components are also referred to as cements. For example, in prism groups which are used as beam splitters, the wedge error unavoidably produced by the cement layer on cementing two prisms can be eliminated by adapting the refractive power. It is thereby possible to improve the imaging quality of the prism group considerably.

Accordingly, there is a need in the industry of adhesives for microscopy and optical elements that address the problems associated with the prior art while maintaining or even improving the high image quality.

SUMMARY OF THE INVENTION

The object of the invention is therefore to provide a composition which overcomes the named disadvantages of the state of the art and has a short curing time accompanied by sufficiently long processing times, is curable at room temperature, provides good adhesion and is excellent for use as adhesive, cement and embedding medium for microscopy.

This object is achieved according to the invention by a composition comprising (A) an epoxide with two or more epoxy groups, (B) a thiol ester with two or more ester groups and two or more thiol groups and/or a thioether with two or more thiol groups and (C) 0.005-2 wt.-%, based on the total weight of the composition, of a tertiary amine which comprises a 5- or 6-membered aliphatic nitrogen heterocycle, wherein the composition contains less than 1 wt.-% primary amine.

The object is further achieved by the use of this composition as adhesive, in particular as cement and as embedding medium for microscopy. The object is also achieved by an optical element in which parts are bonded to each other by the composition according to the invention.

Surprisingly, the composition according to the invention offers a short curing time accompanied at the same time by a sufficiently long processing time, wherein there is already a complete full cure at room temperature and the composition has excellent adhesion. The composition according to the invention is thus suitable in particular as adhesive. In addition, surprisingly, a very good embedding of samples to be investigated microscopically, in particular biological samples, is possible with the composition according to the invention, an excellent image quality is achieved in the microscopic investigation of these samples and the composition according to the invention can be used very well as cement.

The developed polymer system is based on the principle of the base-catalyzed ring opening of epoxides with mercaptans. Here, epoxides, also referred to as epoxy resins, are polymerized with thiols as hardener component. As a rule, epoxy resins can only be cured with mercaptans from temperatures of about 80° C. However, if amines are added as basic catalysts, curing is already possible at room temperature.

The use of amines and mercaptans as crosslinker for curing epoxides is known. Here, the mercaptan component takes over the task of a co-crosslinking flexibilizer. There are adhesive systems with three components, consisting of epoxy resins, mercaptan flexibilizers and amine hardeners. The three components must be stored separately since mixtures of primary amines and mercaptans are not storage-stable. Polysulfides, also called thioplasts, are used as established mercaptan flexibilizers in adhesive formulations.

In contrast, the developed polymer system dispenses with the primary amines customary as hardener component in epoxy resin adhesives. The curing of the epoxides takes place exclusively with multi-functional mercaptans, wherein the tertiary amines function as catalysts. Mixtures of mercaptans with tertiary amines in a catalytic quantity are sufficiently storage-stable at room temperature, as our investigations have shown. It is thus possible to formulate two-component adhesives, in which the hardener component is a polythiol, with a tertiary amine as catalyst.

In the composition according to the invention, component (C), the tertiary amine which comprises an aliphatic nitrogen heterocycle based on a 5- or 6-membered ring, i.e. the pyrrolidine or piperidine derivatives, in particular N-alkylpyrrolidine derivatives or N-alkylpiperidine derivatives, which is contained in the composition according to the invention in catalytic quantities, has a central role. This cycloaliphatic tertiary amine has a sufficiently high basicity and nucleophilicity to catalyze the ring opening of the epoxides with the mercaptans but it undergoes no undesired secondary reactions, for example with the epoxide. Moreover, the composition according to the invention comprises less than 1 wt.-% primary amine, preferably less than 0.1 wt.-%, in order to avoid such secondary reactions, in particular with the epoxides. Surprisingly, the desired property profile in the sense of a sufficiently long processing time and a short setting time of the composition during the polymerization can be achieved with the tertiary amines based on a 5- or 6-membered aliphatic nitrogen heterocycle used in combination with the thiol esters used which, because of the ester grouping, have sufficient reactivity of the SH group.

The epoxy compound used, the thiol ester (mercaptan ester) and the tertiary amine are in each case organic compounds, i.e. an organic epoxy compound, an organic thiol ester and an organic tertiary amine are used. Within the meaning of the invention, as is customary in the state of the art, by an organic compound is meant a carbon-containing chemical compound.

By "containing a compound" such as e.g. an epoxy compound, a thiol ester or a tertiary amine is meant, as is customary, that the composition can contain or comprise one or more of these compounds. In this sense, the invention relates to a composition comprising one or more epoxy compounds in each case with two or more epoxy groups, one or more thiol esters in each case with two or more ester groups and two or more thiol groups and/or one or more thioethers in each case with two or more thiol groups and 0.005-2 wt.-%, based on the total weight of the composition, of one or more tertiary amines which comprises a 5- or 6-membered aliphatic nitrogen heterocycle, wherein the composition contains less than 1 wt.-%, based on the total weight of the composition, of primary amine.

As is also customary in the state of the art, by an aliphatic compound is meant an organic chemical compound which is not aromatic. The aliphatic compound can be saturated or unsaturated. Epoxides, thiol esters, thioethers and amines are known to a person skilled in the art, as are isocyanates and thiourethanes. In this sense, a thiol ester is a compound which contains a thiol group (—SH) and an ester grouping (—COOR), a thioether contains the grouping RSR' (R and R'=alkyl or aryl) and a thiourethane contains the group RSC(NH)OR', as is used in the case of a pre-polymeric/oligomeric precursor.

Within the meaning of the invention, by a polymer is meant an organic compound which is built up from repeating units of monomers.

Within the meaning of the invention, a photolatent base is a photolatent base compound according to claim 1 of EP 2 145 231 B1. The content of EP 2 145 231 B1 is hereby incorporated in the present application by reference. Claim 1 of EP 2 145 231 B1 is reproduced below:

A photolatent base compound of the formula (I), (II) or (III)

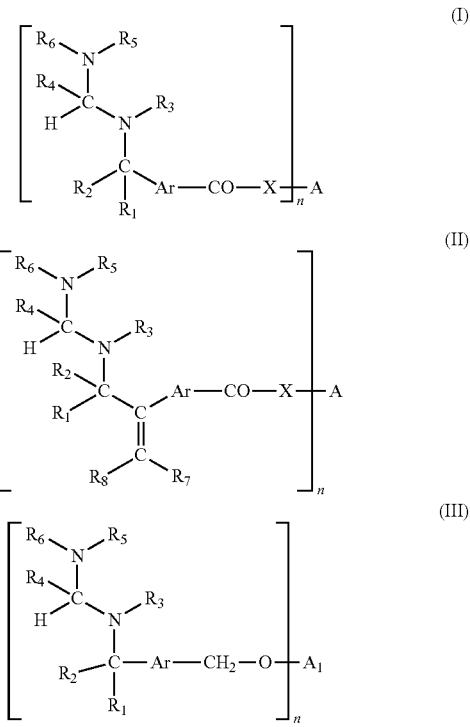

wherein
    Ar is phenylene, biphenylene, naphthylene, anthrylene or anthraquinonylene all of which are unsubstituted or are substituted by one or more $C_1$-$C_4$-alkyl, $C_2$-$C_4$-alkenyl, CN, $OR_{11}$, $SR_{11}$, $CH_2OR_{11}$, $COOR_{12}$, $CONR_{12}R_{13}$ or halogen;

$R_1$, $R_2$, $R_7$ and $R_8$ independently of one another are hydrogen or $C_1$-$C_6$-alkyl; $R_3$ and $R_5$ together form a $C_2$-$C_6$-alkylene bridge which is unsubstituted or substituted by one or more $C_1$-$C_4$-alkyl;

$R_4$ and $R_6$ together form a $C_2$-$C_6$-alkylene bridge which is unsubstituted or substituted by one or more $C_1$-$C_4$-alkyl;

$R_{11}$ is hydrogen, $C_1$-$C_6$-alkyl or phenyl;

$R_{12}$ and $R_{13}$ independently of one another are hydrogen, phenyl, $C_1$-$C_{18}$-alkyl, $C_1$-$C_{18}$-alkyl which is interrupted by one or more O; or $R_{12}$ and $R_{13}$ are

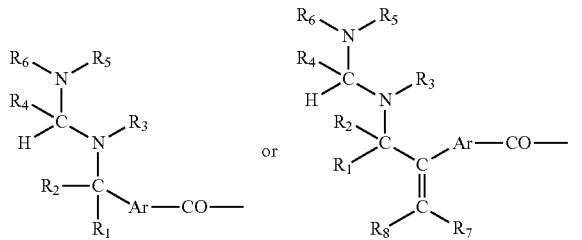

n is 1-10;

X is a direct bond, O, S or $NR_{10}$;

A, if n is 1, is uninterrupted $C_1$-$C_{18}$-alkyl or $C_1$-$C_{18}$-alkyl which is interrupted by one or more O or $N(R'_{13})$ and which uninterrupted or interrupted $C_1$-$C_{18}$-alkyl is unsubstituted or is substituted by one or more $C_1$-$C_{18}$-alkyl, $C_1$-$C_6$-hydroxyalkyl, CN, $OR_{11}$, $SR_{11}$, $NR_{12}R_{13}$, $COOR_{12}$, $OCOR_{14}$ or halogen; or A is $C_2$-$C_{18}$-alkenyl or is $C_3$-$C_{18}$-alkenyl which is interrupted by one or more O and which $C_2$-$C_{18}$-alkenyl or interrupted $C_3$-$C_{18}$-alkenyl is unsubstituted or is substituted by one or more $C_1$-$C_8$-alkyl, $C_1$-$C_6$-hydroxyalkyl, CN, $OR_{11}$, $SR_{11}$, $NR_{12}R_{13}$, $COOR_{12}$, halogen or $C_7$-$C_{15}$-aralkyl; or A, if n is 1, is a group

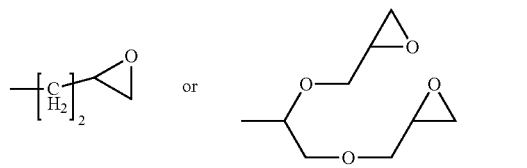

or

A, if n is 1, denotes a group

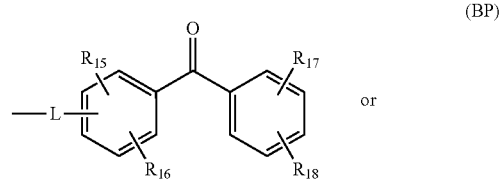
(BP)

or

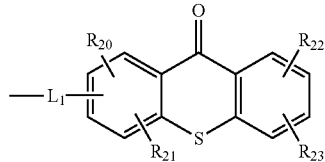
(TX)

or, if X is O, additionally X-A denotes $X^-Y^+$;

A, if n is greater than 1, is an n-valent saturated or unsaturated $C_2$-$C_{50}$-hydrocarbon radical, which optionally is interrupted by one or more O, S, $N(R'_{13})$, phenylene, naphthylene,

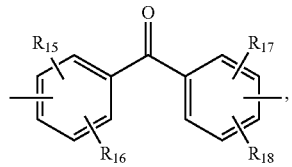

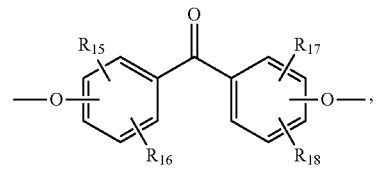

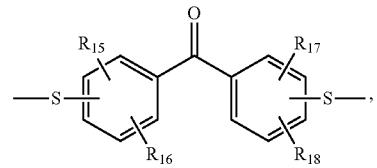

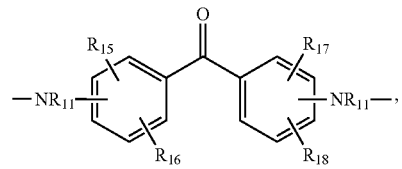

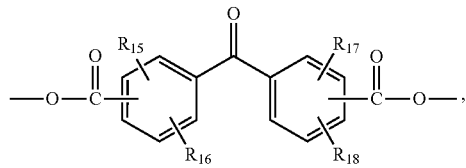

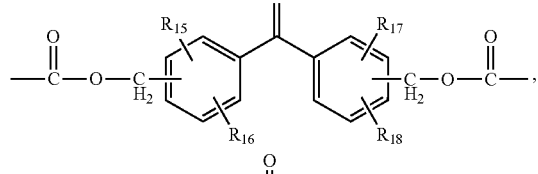

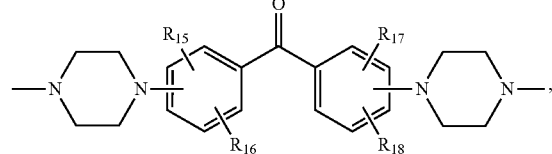

-continued

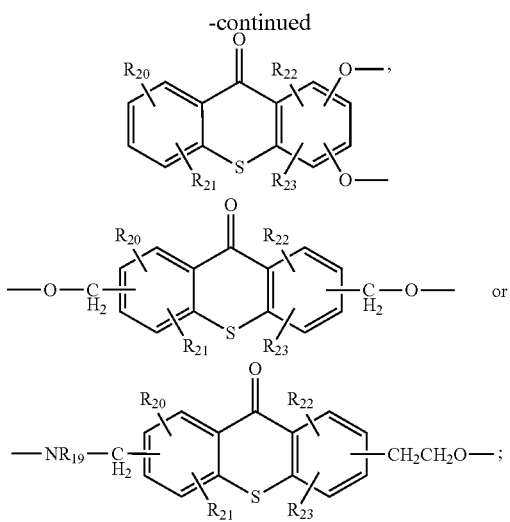

and which uninterrupted or interrupted n-valent saturated or unsaturated $C_2$-$C_{50}$-hydrocarbon radical is unsubstituted or is substituted by one or more $C_1$-$C_8$-alkyl, $C_1$-$C_6$-hydroxyalkyl, CN, $OR_{11}$, $SR_{11}$, $NR_{12}R_{13}$, $COOR_{12}$ or halogen;

or A, if X is $NR_{10}$, is an n-valent polyalkylene-imine; wherein the n-valent polyalkylene-imine is uninterrupted or interrupted by one or more (CO), (CO)O or double bonds and wherein the uninterrupted or interrupted n-valent polyalkylene-imine is unsubstituted or substituted by

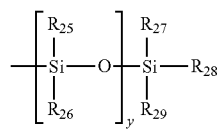

or, if X is O, additionally one or more X-A denote $X'_n$, $Y^{n+}$ or $X^-_n nY^+$;

y is an integer from 1-20;
z is an integer from 1-8;
$R'_{13}$ has one of the meanings as given for $R_{12}$ and $R_{13}$ or is a group (TX);
$R_{10}$ has one of the meanings as given for A, if n is 1;
$A_1$, if n is 1, is hydrogen, $C_1$-$C_{18}$-alkanoyl, $C_2$-$C_{18}$-alkanoyl which is interrupted by one or more O and/or CO and which uninterrupted or interrupted $C_2$-$C_{18}$-alkanoyl is unsubstituted or substituted by one or more $C_1$-$C_4$-alkyl, $C_2$-$C_4$-alkenyl, phenyl, CN, $OR_{11}$, $SR_{11}$, $NR_{12}R_{13}$, $COOR_{12}$ or halogen; or said uninterrupted or interrupted $C_2$-$C_{18}$-alkanoyl is substituted by $C_6$-$C_{10}$-aryl which is unsubstituted or substituted by one or more $C_1$-$C_4$-alkyl, $C_2$-$C_4$-alkenyl, CN, $OR_{11}$, $SR_{11}$, $NR_{12}R_{13}$ or halogen;

or $A_1$ is $C_3$-$C_{18}$-alkenoyl which is unsubstituted or substituted by one or more $C_1$-$C_4$-alkyl, $C_2$-$C_4$-alkenyl, CN, $OR_{11}$, $SR_{11}$, $NR_{12}R_{13}$, $COOR_{12}$, halogen or by $C_6$-$C_{10}$-aryl which is unsubstituted or substituted by one or more $C_1$-$C_4$-alkyl, $C_2$-$C_4$-alkenyl, CN, $OR_{11}$, $SR_{11}$, $NR_{12}R_{13}$ or halogen;

$C_2$-$C_{18}$-alkylaminocarbonyl, which is unsubstituted or substituted by one or more $C_1$-$C_4$-alkyl, $C_2$-$C_4$-alkenyl, CN, $OR_{11}$, $SR_{11}$, $NR_{12}R_{13}$, $COOR_{12}$ or halogen;

$C_6$-$C_{20}$-arylaminocarbonyl, which is unsubstituted or substituted by one or more $C_1$-$C_4$-alkyl, $C_2$-$C_4$-alkenyl, $OR_{11}$, $NR_{12}R_{13}$ or halogen; $C_7$-$C_{20}$-arylalkylaminocarbonyl which is unsubstituted or substituted by one or more $C_1$-$C_4$-alkyl, $C_2$-$C_4$-alkenyl, $OR_{11}$, $NR_{12}R_{13}$ or halogen;

$C_7$-$C_{15}$-aroyl or $C_5$-$C_{15}$-heteroaroyl, both of which are unsubstituted or substituted by one or more $C_1$-$C_4$-alkyl, $C_2$-$C_4$-alkenyl, CN, $OR_{11}$, $SR_{11}$, $NR_{12}R_{13}$ or halogen;

or
$A_1$, if n is 1, denotes a group

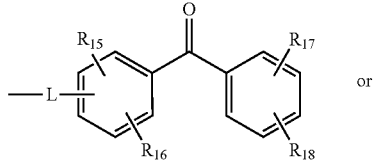 (BP)

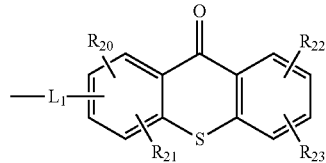 (TX)

$A_1$, if n is greater than 1, is an n-valent $C_2$-$C_{30}$-alkanoyl which optionally is interrupted by one or more O and which uninterrupted or interrupted $C_2$-$C_{30}$-alkanoyl is unsubstituted or is substituted by one or more $C_1$-$C_4$-alkyl, $C_2$-$C_4$-alkenyl, CN, $OR_{11}$, $SR_{11}$, $NR_{12}R_{13}$, $COOR_{12}$, or halogen;

an n-valent $C_8$-$C_{20}$-aroyl or $C_6$-$C_{20}$-heteroaroyl both of which are unsubstituted or substituted by one or more $C_1$-$C_4$-alkyl, $C_2$-$C_4$-alkenyl, CN, $OR_{11}$, $SR_{11}$, $NR_{12}R_{13}$, $COOR_{12}$ or halogen;

an n-valent $C_{10}$-$C_{20}$-aralkanoyl which is unsubstituted or substituted by one or more $C_1$-$C_4$-alkyl, $C_2$-$C_4$-alkenyl, CN, $OR_{11}$, $SR_{11}$, $NR_{12}R_{13}$, $COOR_{12}$ or halogen; or is an n-valent $C_1$-$C_{30}$-alkylaminocarbonyl, which is unsubstituted or substituted by one or more $C_1$-$C_4$-alkyl, $C_2$-$C_4$-alkenyl, CN, $OR_{11}$, $SR_{11}$, $NR_{12}R_{13}$, $COOR_{12}$ or halogen, wherein said unsubstituted or substituted n-valent $C_1$-$C_{30}$-alkylaminocarbonyl optionally consists of several mono-valent $C_1$-$C_{30}$-alkylaminocarbonyl groups which are linked via dimers or trimers of isocyanates or derivatives thereof; or is an n-valent $C_6$-$C_{20}$-arylaminocarbonyl, which is unsubstituted or substituted by one or more $C_1$-$C_4$-alkyl, $C_2$-$C_4$-alkenyl, CN, $OR_{11}$, $SR_{11}$, $NR_{12}R_{13}$, $COOR_{12}$ or halogen;

or
$A_1$, if n is greater than 1, denotes a group

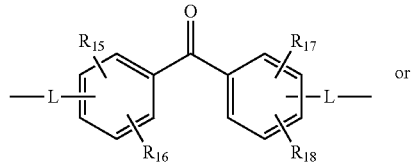 (BP')

-continued

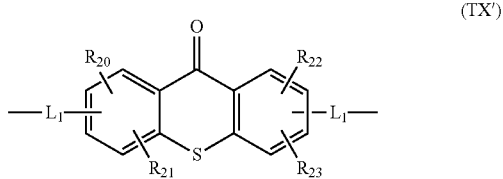
(TX')

L is a direct bond; unsubstituted $C_1$-$C_{20}$-alkylene, $C_1$-$C_{20}$-alkylene which is substituted by phenyl or one or more OH; $C_1$-$C_{20}$-alkylene which is interrupted by one or more O, S, O(CO), (CO)O;
or is $C_1$-$C_{20}$-alkylene-O—(CO), $C_1$-$C_{20}$-alkylene-N($R_{19}$)(CO), $C_1$-$C_{20}$-alkylene-S, $C_1$-$C_{20}$-alkylene-O, $C_1$-$C_{20}$-alkylene-(N$R_{19}$) or $C_1$-$C_{20}$-alkylene-(CO)—N($R_{19}$), where in the groups $C_1$-$C_{20}$-alkylene-O(CO), $C_1$-$C_{20}$-alkylene-N($R_{19}$)(CO), $C_1$-$C_{20}$-alkylene-S, $C_1$-$C_{20}$-alkylene-O, $C_1$-$C_{20}$-alkylene-(N$R_{19}$) and $C_1$-$C_{20}$-alkylene-(CO)—N($R_{19}$), the linkage to the benzophenone group is intended to be via the heteroatom N, S or O or via the CO group; or
L is (CO)-Q;
Q is a direct bond, $C_1$-$C_8$-alkylene or $C_1$-$C_8$-alkylene which is interrupted by one or more O;
$L_1$ is a direct bond, CO; unsubstituted $C_1$-$C_{20}$-alkylene, $C_1$-$C_{20}$-alkylene which is substituted by phenyl or one or more OH; $C_1$-$C_{20}$-alkylene which is interrupted by one or more O, S or N$R_{24}$; $C_1$-$C_{20}$-alkylene which is interrupted by one or more O, S or N$R_{24}$ and is substituted by OH;
or is unsubstituted $C_1$-$C_{20}$-alkylene-O—(CO) or $C_1$-$C_{20}$-alkylene-O—(CO) which is substituted by OH, or is $C_1$-$C_{20}$-alkylene-O—(CO), wherein the alkylene is interrupted by one or more O; $C_1$-$C_{20}$-alkylene-N($R_{19}$)(CO), $C_1$-$C_{20}$-alkylene-S, $C_1$-$C_{20}$-alkylene-O, $C_1$-$C_{20}$-alkylene-(N$R_{19}$) or $C_1$-$C_{20}$-alkylene-(CO)—N($R_{19}$), wherein the groups $C_1$-$C_{20}$-alkylene-O—(CO) or $C_1$-$C_{20}$-alkylene-O—(CO) which is substituted by OH, or is $C_1$-$C_{20}$-alkylene-O—(CO), wherein the alkylene is interrupted by one or more O; $C_1$-$C_{20}$-alkylene-N($R_{19}$)(CO), $C_1$-$C_{20}$-alkylene-S, $C_1$-$C_{20}$-alkylene-O, $C_1$-$C_{20}$-alkylene-(N$R_{19}$) or $C_1$-$C_{20}$-alkylene-(CO)—N($R_{19}$), the linkage to the thioxanthone group is intended to be via the heteroatom N, S or O or via the CO group; or
$L_1$ is (CO)—$C_1$-$C_{20}$-alkylene-O, where the linkage to the thioxanthone group is intended to be via the O atom; or
$L_1$ is (CO)-Q;
Y is an n-valent cationic counter ion;
$R_{14}$ is —CH=$CH_2$ or —C($CH_3$)=$CH_2$;
$R_{15}$, $R_{16}$, $R_{17}$ and $R_{18}$ independently of one another are hydrogen, halogen, $C_1$-$C_{12}$-alkyl, O$R_{11}$, S$R_{11}$, N$R_{12}R_{13}$, or (CO)O$R_{11}$;
$R_{19}$ is hydrogen or $C_1$-$C_6$-alkyl;
$R_{20}$, $R_{21}$, $R_{22}$ and $R_{23}$ independently of one another have one of the meanings as defined for $R_{15}$, $R_{16}$, $R_{17}$ and $R_{18}$;
$R_{24}$ is hydrogen, $C_1$-$C_{10}$-alkyl or $C_1$-$C_{10}$-alkyl which is substituted by OH; and
$R_{25}$, $R_{26}$, $R_{27}$, $R_{28}$ and $R_{29}$ independently of one another are $C_1$-$C_4$-alkyl.

Diglycidyl ethers are preferred as epoxides according to the invention because within them the epoxy group is sufficiently reactive and the steric hindrance is sufficiently low for opening by the thiol ester. Particularly preferred epoxides are bisphenol A diglycidyl ether (Araldite F, Rutapox 0162), bisphenol F diglycidyl ether (Rutapox 0158), Nanopox F 440 (bisphenol A/F diglycidyl ether with approx. 40% nanoscale $SiO_2$), colourless resin adhesive 52A (bisphenol A/F diglycidyl ether with bound butadiene-acrylonitrile copolymer), bisphenol A propoxylate diglycidyl ether, bisphenol A ethoxylate diglycidyl ether, bisphenol (hydrogenated) A diglycidyl ether (Epalloy 5000), resorcinol diglycidyl ether, 1,4-cyclohexane dimethanol diglycidyl ether (Erisys GE-22), 1,4-butanediol diglycidyl ether, 1,6-hexanediol diglycidyl ether, neopentyl glycol diglycidyl ether, dipropylene glycol diglycidyl ether, polypropylene glycol diglycidyl ether, trimethylolpropane triglycidyl ether, trimethylolethane triglycidyl ether, pentaerythritol polyglycidyl ether (IPDX CL-16) and 1,3-xylylene tetraglycidyl amine (Erisys GA-240). Bisphenol A diglycidyl ether and bisphenol F diglycidyl ether are most preferred.

Furthermore, it can be advantageous to add an epoxidized phenol novolac resin (e.g. Epalloy 8330) to the epoxy component (epoxy compound).

Mercaptoacetates, 2-mercaptopropionates and 3-mercaptopropionates are preferred as thiol esters because these compounds have a particularly suitable reactivity in combination with the tertiary aliphatic amines according to the invention, with the result that long processing times and short curing phases are made possible. Thiol esters with 3 or more thiol groups and 3 or more ester groups are further preferred. Particularly preferred are pentaerythritol tetra(3-mercaptopropionate) (PTMP), trimethylolpropane tri(3-mercaptopropionate) (TPMP), ethylene glycol di(3-mercaptopropionate) (GDMP), pentaerythritol tetra (mercaptoacetate) (PTMA), trimethylolpropane tri (mercaptoacetate) (TPMA), ethylene glycol di(mercaptoacetate) (GDMA), tris [2-(3-mercaptopropionyloxy)ethyl] isocyanurate (TEMPIC) and tris-[2-(2-mercaptopropionyloxy)ethyl] isocyanurate (TETLIC). Among these, pentaerythritol tetra(3-mercaptopropionate) has proven to be particularly advantageous. The combination of bisphenol A diglycidyl ether and pentaerythritol tetra(3-mercaptopropionate) and the combination of bisphenol F diglycidyl ether and pentaerythritol tetra(3-mercaptopropionate) are particularly preferred. As alternatives to the described polyesters, aliphatic or cycloaliphatic thiols with thioether structures, e.g. MR7 B (4-mercaptomethyl-3,6-dithia-1,8-octanedithiol) or MR10 B (Manufacturer: Mitsui Toatsu Chemicals), can also be used for specific applications. These thioether thiols are suitable in particular for highly refractive optical adhesives and highly refractive embedding media for microscopy, refractive powers when cured $n_e$(20° C.)≥1.60. Aliphatic dimercaptan compounds such as e.g. bis-(2-mercaptoethyl) ether or bis-(2-mercaptoethyl) sulfide can be added as reactive diluent.

In the composition according to the invention, as component (C), a tertiary amine is used which comprises a 5- or 6-membered aliphatic nitrogen heterocycle. The aliphatic nitrogen heterocycle is preferably saturated. Preferred are optionally substituted N—($C_1$-$C_4$)-alkylpyrrolidine, optionally substituted N—($C_1$-$C_4$)-alkylpyrrolidone, N—($C_1$-$C_4$)-alkylpiperidine, N—($C_1$-$C_4$)-alkylpiperazine, optionally substituted N,N—($C_1$-$C_4$)-dialkylpiperazine, optionally substituted N—($C_1$-$C_4$)-alkylmorpholine, optionally substituted 1,4-diazabicyclo[2.2.2]octane (DABCO), optionally substituted 1,5-diazabicyclo[4.3.0]non-5-ene (DBN) and optionally substituted 1,8-diazabicyclo[5.4.0]undec-7-ene (DBU). ($C_1$-$C_4$)-alkyl represents an aliphatic group with 1-4 carbon atoms, i.e. methyl, ethyl, propyl, isopropyl, n-butyl, iso-butyl, sec-butyl and tert-butyl. The alkyl groups are preferably unsubstituted or substituted with a hydroxy group.

The following compounds are particularly preferred as tertiary amines with a 5- or 6-membered aliphatic nitrogen heterocycle: 1-(2-hydroxyethyl)pyrrolidine, 1-(2-hydroxyethyl)pyrrolidone, 1-(2-hydroxyethyl)piperidine, 1-ethylpiperazine, 1-(2-hydroxyethyl)piperazine, 1,4-bis-(2-hydroxyethyl)piperazine, 4 (2 hydroxyethyl)morpholine, 1,4-diazabicyclo[2.2.2]octane (DABCO), 1,5-diazabicyclo[4.3.0]non-5-ene (DBN) and 1,8-diazabicyclo[5.4.0]undec-7-ene (DBU).

The rate of the reaction between epoxy compound and thiol ester in the composition according to the invention and thus the processing time and curing time are controlled by the basicity and the concentration of the added tertiary amine. For a sufficient processing time on the one hand and a short curing time on the other hand, 0.005-2 wt.-% of the tertiary amine with the 5- or 6-membered aliphatic nitrogen heterocycle have proven to be suitable. 0.01-2 wt.-% of the tertiary amine is preferred and in particular 0.02-1.5 wt.-%. In the case of less strong bases, a somewhat higher quantity is advantageous within this range and, in the case of the stronger bases, a somewhat smaller quantity is advantageous.

The basicity of tertiary amines as a measure for the catalytic effectiveness can be affected by the steric availability of the electron pair on the amine nitrogen. The relative reactivity of tertiary amines which are suitable for the amine-catalyzed thiol curing of epoxides was investigated on a model adhesive consisting of Araldite F and PTMP. This yielded:
a) with strong amine bases, amine concentration in the blended adhesive 0.2%
DBN: reactivity 1.0
DBU: reactivity 1.0
DABCO: reactivity 0.2
b) amines with average basicity, amine concentration in the blended adhesive 2%
1-(2-Hydroxyethyl)pyrrolidine: reactivity 1.0
1-Methylimidazole: reactivity 0.24
1-Ethylpiperazine: reactivity 0.20
4-(2-Hydroxyethyl)morpholine: reactivity 0.04

Against this background, it is particularly preferred to use 0.005-0.3 wt.-%, based on the total weight of the composition, in particular 0.01-0.2 wt.-%, one or more tertiary amines, selected from the group consisting of 1,5-diazabicyclo[4.3.0]non-5-ene (DBN), 1,8-diazabicyclo[5.4.0]undec-7-ene (DBU) and 1,4-diazabicyclo[2.2.2]octane (DABCO) or to use 0.3-2 wt.-%, based on the total weight of the composition, in particular 0.5-1 wt.-%, one or more tertiary amines, selected from the group consisting of 1-(2-hydroxyethyl)pyrrolidine, 1-(2-hydroxyethyl)pyrrolidone, 1-(2-hydroxyethyl)piperidine, 1-ethylpiperazine, 1-(2-hydroxyethyl)piperazine, 1,4-bis-(2-hydroxyethyl)piperazine, 1-methylimidazole and 4-(2-hydroxyethyl)morpholine.

A further desired property of adhesive compositions and embedding media is that as little stress as possible arises in the cured composition. The compositions according to the invention made from epoxy compounds, thiol esters and the cycloaliphatic tertiary amine as described above can be designed as particularly low stress formulations if an oligomer is added to the composition before the polymerization. Within the meaning of the invention, by an oligomer is meant an organic compound which is built up from repeating units of monomers, wherein the number average number of monomers (sum of all monomers) is 3-100, preferably 5-80, in particular 3-45, further preferably 5-25, particularly preferably 7-15. This oligomer is also referred to as pre-polymer below. It is assumed that the reduction in stresses is based on the fact that the added oligomers reduce shrinkage during curing. Rheological and thermoanalytical investigations established that the oligomers have the advantage that the curing reaction with the epoxy component starts more uniformly compared with monomeric thiols. The reason for this may be the reactivity distribution of the individual thiol functions given by the pre-polymeric structure.

In addition, with the additional oligomer, the viscosity can be adapted to the desired intended use. It is preferred that the composition contains 10-50 wt.-%, based on the total weight of the composition, of oligomers, in particular 20-40 wt.-%, based on the total weight of the composition. In a preferred embodiment of the composition according to the invention, the oligomer can be contained in addition to the components (A) to (C) described above or the thiol ester (B) can be the oligomer.

The oligomer, which is also referred to below as pre-polymer, is preferably an oligomeric thiourethane. Thiourethanes are known to a person skilled in the art. They can be prepared from a thiol and an isocyanate. According to the invention, oligomeric thiourethanes are preferred which can be obtained by reacting at least one thiol ester which comprises two or more ester groups and two or more thiol groups and/or can be obtained by reacting at least one thioether which comprises two or more thiol groups with at least one di- or polyisocyanate, wherein the oligomeric thiourethane comprises two or more free thiol groups. The number average sum of the number of the thiol and isocyanate monomers contained in the oligomer is preferably 3-100, further preferably 5-80, in particular 3-45, further preferably 5-25 and particularly preferably 7-15. In this sense, the oligomer PTMP-XDI-PTMP-XDI-PTMP would comprise 5 monomers.

For the preparation of the oligomeric thiourethane, the thiol ester is preferably used in excess compared with the isocyanate, in order to have free thiol groups in the oligomeric thiourethane and in order to avoid polymeric structures. The oligomeric thiourethane preferably comprises 4 or more, in particular 6 or more and particularly preferably 8 or more and further preferably 10 or more (free) thiol groups. The number average of the molar mass of the oligomer is preferably 1,000-15,000, in particular 1,500-8,000, particularly preferably 2,000-5,000.

In a preferred embodiment, the thiol ester and/or the thioether of the composition according to the invention is an oligomeric thiourethane. The oligomeric thiourethane can preferably be obtained by reacting at least one thiol ester which comprises two or more ester groups and two or more thiol groups with at least one di- or polyisocyanate, wherein the oligomeric thiourethane comprises two or more free thiol groups and/or preferably by reacting at least one thioether which comprises two or more thiol groups with at least one di- or polyisocyanate, wherein here too the oligomeric thiourethane comprises two or more free thiol groups.

In a further preferred embodiment, the thiol ester of the composition according to the invention represents a mixture of two or more oligomeric thiourethanes. The oligomeric thiourethanes can preferably be obtained in each case as described above.

The number average of the monomers contained in the oligomeric thiourethane is preferably 3-100, further preferably 5-80, in particular 3-45, further preferably 5-25, particularly preferably 7-15. The proportion of the oligomeric thiourethane or of the oligomeric thiourethanes, based on the total weight of the composition, is 10-60 wt.-%, preferably 10-50 wt.-%, in particular 20-50 wt.-%.

Preferred are oligomers or oligomeric thiourethanes made from pentaerythritol tetra(3-mercaptopropionate) (PTMP) with xylylene diisocyanate (XDI), made from pentaerythritol tetra(3-mercaptopropionate) with norbornyl diisocyanate (NBDI) or made from pentaerythritol tetra(3-mercaptopropionate) with isophorone diisocyanate (IPDI) as well as oligomers made from trimethylolpropane tri(3-mercaptopropionate) (TPMP) with xylylene diisocyanate, made from trimethylolpropane tri(3-mercaptopropionate) with norbornyl diisocyanate (NBDI) or made from trimethylolpropane tri(3-mercaptopropionate) with isophorone diisocyanate (IPDI). In these oligomers, the ratio of mercaptopropionate and diisocyanate is preferably 20:1 to 5:1, so that diisocyanate groups are completely reacted.

Example PTMP/XDI:
PTMP molecular weight 488 g/mol, 4 SH groups
XDI molecular weight 188 g/mol, 2 NCO groups
Preparation of the oligomers: the polythiol is completely reacted with the isocyanate in stoichiometric excess under inert gas. Monitoring by IR spectroscopy (NCO band at approx. 2260 cm$^{-1}$). When an NCO band can no longer be detected in the IR spectrum, as a rule the proportion of free isocyanate is <0.05 wt.-%.
Pre-polymer PTMP/XDI 100+10: 13.0% of the SH groups are reacted.
Pre-polymer PTMP/XDI 100+15: 19.5% of the SH groups are reacted.
Pre-polymer PTMP/XDI 100+20: 26.0% of the SH groups are reacted.

The ratio of PTMP to XDI is related to the viscosity of the pre-polymers/oligomers which are produced during the reaction, which thus significantly influence the viscosity of the resulting adhesive.

A composition containing the following has proven to be particularly advantageous:
(A) bisphenol A diglycidyl ether and/or bisphenol F diglycidyl ether,
(B) 10-50 wt.-%, in particular 20-40 wt.-%, based on the total weight of the composition, of a thiol ester in the form of one or more oligomeric thiourethanes, which can be obtained in each case from pentaerythritol tetra(3-mercaptopropionate) (PTMP) and/or trimethylolpropane tri (3-mercaptopropionate) (TPMP) with xylylene diisocyanate (XDI), norbornyl diisocyanate (NBDI) and/or isophorone diisocyanate (IPDI), wherein each oligomeric thiourethane comprises two or more free thiol groups, and
(C) 0.005-0.3 wt.-%, based on the total weight of the composition, one or more tertiary amines, selected from the group consisting of 1,5-diazabicyclo[4.3.0]non-5-ene (DBN), 1,8-diazabicyclo[5.4.0]undec-7-ene (DBU) and 1,4-diazabicyclo[2.2.2]octane (DABCO) or 0.3-2 wt.-%, based on the total weight of the composition, one or more tertiary amines, selected from the group consisting of 1-(2-hydroxyethyl)pyrrolidine, 1-(2-hydroxyethyl)pyrrolidone, 1-(2-hydroxyethyl)piperidine, 1-ethylpiperazine, 1-(2-hydroxyethyl)piperazine, 1,4-bis-(2-hydroxyethyl)piperazine, 1-methylimidazole and 4-(2-hydroxyethyl)morpholine,
wherein the composition contains less than 1 wt.-% primary amine.

A composition has also proven to be advantageous which, in addition to the components (A)-(C) described above, additionally comprises an oligomer, in particular the oligomeric thiourethane described above. Particularly advantageously, this is a composition containing, preferably consisting of,
(A) bisphenol A diglycidyl ether and/or bisphenol F diglycidyl ether,
(B) pentaerythritol tetra(3-mercaptopropionate) and/or trimethylolpropane tri(3-mercaptopropionate) and
(C) 0.005-2 wt.-%, based on the total weight of the composition, 1-(2-hydroxyethyl)pyrrolidine, 1-(2-hydroxyethyl)pyrrolidone, 1-(2-hydroxyethyl)piperidine, 1-ethylpiperazine, 1-(2-hydroxyethyl)piperazine, 1,4-bis-(2-hydroxyethyl)piperazine, 1-methylimidazole, 4-(2-hydroxyethyl)morpholine, 1,4-diazabicyclo [2.2.2]octane (DABCO), 1,5-diazabicyclo[4.3.0]non-5-ene (DBN) and/or 1,8-diazabicyclo[5.4.0]undec-7-ene (DBU), and optionally
(D) 10-50 wt.-%, in particular 20-40 wt.-%, based on the total weight of the composition, of an oligomer made from pentaerythritol tetra(3-mercaptopropionate) (PTMP) and/or trimethylolpropane tri(3-mercaptopropionate) (TPMP) with xylylene diisocyanate (XDI), norbornyl diisocyanate (NBDI) and/or isophorone diisocyanate (IPDI),
wherein the composition contains less than 1 wt.-%, preferably less than 0.1 wt.-%, primary amine.

In an advantageous embodiment, the composition according to the invention contains 10-85 wt.-%, in particular 30-70 wt.-%, preferably 40-60 wt.-%, based on the total weight of the composition, of epoxy compound with two or more epoxy groups, and 30-70 wt.-%, based on the total weight of the composition, preferably 40-60 wt.-% of thiol ester with two or more ester groups and two or more thiol groups.

In a further embodiment of the composition according to the invention, this contains no further compounds which could undergo a ring-opening reaction with the epoxide. In particular, it is preferred for the composition according to the invention to contain less than 1 wt.-%, preferably less than 0.1 wt.-%, based on the total weight of the composition, alcohol and/or phenol.

In a further advantageous embodiment, the composition is UV curable and additionally also contains the following components: 0.5-2 wt.-%, based on the total weight of the composition, of a photolatent base and a photoinitiator. Component (C) is preferably a photolatent base and contained in the composition in a quantity of 0.5-2 wt.-%, based on the total weight of the composition.

As explained above, within the meaning of the invention, by a photolatent base is meant the photolatent base compound according to claim 1 of EP 2 145 231 B1. Within the meaning of the invention, a photoinitiator is a chemical compound which decomposes into reactive fractions through the absorption of light. In the composition according to the invention, these reactive fractions then detach the protective group from the photolatent base, with the result that a strongly basic amidine structure forms from the photolatent base which, as base, catalyzed the polymerization reaction between the epoxide and the SH group of the thiol ester. In this way, the amine-catalyzed thiol reaction with the epoxide is accelerated locally in the area of the action of UV light, whereby the curing time of the composition is greatly shortened.

Further to the photoinitiator, a dye can be contained. The dye is added to the resin component (A) in order to make the UV activation visible. When Sudan Blue is used, a colour change from blue to yellow is observed through irradiation with UV light (365 nm). The process is irreversible. It can serve to make the UV activation of the adhesive visible.

It was established that there are no significant differences in the polymers and their usage properties between darkness curing and curing after UV activation of the composition according to the invention.

Preferably an optionally substituted 5-(carbonylarylmethyl)-1,5-diazabicyclo[4.3.0]nonane or an optionally substituted 8-(carbonylarylmethyl)-1,8-diazabicyclo[5.4.0]undecane is used as photolatent base. As component (C) and as photolatent base, optionally substituted 5-(4-alkoxycarbonylbenzylmethyl)-1,5-diazabicyclo[4.3.0]nonane or an optionally substituted 8-(4-alkoxycarbonylbenzylmethyl)-1,8-diazabicyclo[5.4.0]undecane are particularly preferred. From these preferred photolatent bases, through irradiation with UV light (light with a wavelength of about 200-450 nm), 1,5-diazabicyclo[4.3.0]non-5-ene (DBN) or 1,8-diazabicyclo[5.4.0]undec-7-ene (DBU) are formed.

Preferred photoinitiators according to the invention are benzophenone and hydroxybenzophenone derivatives such as e.g. Darocur 1173 (2-hydroxy-2-methyl-1-phenyl-propane-1-one) and Irgacure 1700 (Darocur 1173+bis-(2,6-dimethoxybenzoyl)-2,4,4-trimethylpentylphosphine oxide). These compounds are preferably used in the composition as component (C) in a quantity of 0.5-2 wt.-%, based on the total weight of the composition, preferably in the component which comprises the epoxide.

When using the composition according to the invention as embedding medium or for bonding glasses, it is advantageous if the composition additionally contains an alkoxysilane. Among other things, the alkoxysilane contributes to the adhesion to the glass, for example between the embedding medium and the regularly used glass of the specimen slide and of the cover glass.

Within the meaning of the invention, an alkoxysilane is a compound of the form $(R^1O)_nSiR^2{}_{3-n}R^3$, wherein n=1-3, preferably n=3, $R^1$ and $R^2$, independently of one another, are aliphatic, cycloaliphatic or aromatic radicals with 1-10 carbon atoms, preferably aliphatic radicals with 1-4 carbon atoms, i.e. methyl, ethyl, propyl, isopropyl, n-butyl, isobutyl, sec-butyl or tert-butyl, and $R^3$ is a polymerizable radical. Preferred for $R^3$ are organic radicals with one or more epoxy or mercaptan group(s). Preferred alkoxysilanes are trialkoxysilanes, in particular those of the formula $(R^1O)_3SiR^3$. Trimethoxysilanes are particularly preferred. The alkoxysilane is preferably contained in the composition in a quantity of 0.3-3 wt.-%, in particular 0.5-2 wt.-%, based on the total weight of the composition.

A particularly good adhesion to the glass is achieved when the alkoxysilane additionally comprises a polymerizable group. As the alkoxysilane is thus incorporated by polymerization, a particularly high adhesion and stability is achieved. The alkoxysilane preferably comprises an epoxy group or a thiol group. 3-Glycidyloxypropyltrimethoxysilane (GLYMO) and 3-mercaptopropyltrimethoxysilane (MTMO) are particularly preferred.

Furthermore, the composition according to the invention can additionally contain plasticizers, solid plasticizers (melting point≥40° C.), synthetic resins (for example Synthetic Resin SK and Synthetic Resin CA); dyes (for example Sudan Blue or Seripas Red) and/or polymers such as for example ethylene vinyl acetate copolymer (EVA). In addition, fillers such as quartz flours (Silbond) and fine-particle silicic acid can be used as additives. Advantageously, phthalic acid polyester, adipic acid polyester and phosphoric acid ester can be used as plasticizer, phenyl benzoate, glycerol tribenzoate, 1,4-cyclohexane dimethanol dibenzoate, pentaerythritol tetrabenzoate, bis(2-hydroxyethyl) terephthalate and triphenyl phosphate can be used as solid plasticizer and ketone resins, aldehyde resins, acrylic resins, polyterpene resins and modified phenolic resins can be used as synthetic resins.

In a preferred embodiment, the composition is a two-component system in which the first component comprises the epoxide (A) and the second component comprises the thiol ester (B) and tertiary amine (C) and optionally the oligomer (D). The composition with UV activation according to the invention is likewise preferably a two-component system in which the first component comprises (A) and (F) and the second component comprises (B), (C) and (E) and optionally (D). The alkoxysilane (G) can be part of the first or second component, provided that it does not react with the other components. If (G) is an epoxide, the first component is to comprise (A), (F) and (G), if (G) is a thiol, the second component is to comprise (B), (C), (E), (G) and optionally (D).

The invention further relates to the use of the composition according to the invention as adhesive, in particular for precision mechanical and optical devices, and the use as embedding medium for microscopy. A preferred use is the use of the composition according to the invention for bonding precision mechanical or optical devices. Here, the additional oligomers (pre-polymers) described above are of interest in particular in order to reduce stresses.

The application of the compositions according to the invention as adhesive formulation preferably takes place in dual cartridges (2+1 parts by volume or 1+1 part by volume) using a static mixing tube. The mixing process of the adhesive is thus made considerably easier for the user. When used as optically functional polymer system for cementing optical components or for embedding microscopic preparations, resin and hardener are predominantly weighed into a clean mixing vessel using a precision balance and then mixed until they are free from streaks. Because of the requirements which exist for the optical adhesive, the fixed mixing ratios predetermined for the use of dual cartridges can often not be realized.

The adhesives conceived of within the framework of the present invention can be prepared with optically functional properties such as defined refractive index, dispersion, high transmittance, low residual fluorescence and lack of stress by using components of optical quality. To achieve such qualities, it can also be necessary to purify the raw materials used, e.g. by molecular distillation in a fine vacuum or by cleaning over activated carbon or over activated aluminium oxide.

A desired refractive index or dispersion (Abbe number) of such adhesives can be adjusted to the desired purpose through the selection of the components used, in particular the radicals thereof. The adaptation of the refractive power of adhesives for optical components (cements), in particular the adaptation of the refractive power to an optical component to be bonded can take place for defined wavelengths (e.g. in the case of optical measuring systems) or in the case of polychromatic applications for a determined wavelength range (e.g. 450 nm-700 nm). In the polychromatic adaptation of the refractive power it is important to match the dispersion (wavelength-dependence of the refractive power) of the cement and optical components to each other as closely as possible. In such cases, a spectral centroid is usually defined, e.g. 546 nm ($n_e$). The dispersion of cements can be controlled through the cement components used since the chemical structure of the monomer substances has a considerable influence on the refractive power and the dispersion. The exact adaptation of the refractive power of (cured) cements to optical components is also referred to as "index matching".

A specific application is the cementing of optical components which partially comprise diffractive, reflective and/or other micro-optical elements on a component surface. For example, if the refractive power is adapted to Δn<0.0005, diffractive structures enclosed in the cement layer are no longer optically recognizable.

Cement components with refractive powers which are as defined as possible should be used for very accurate index matching. The resin component of the cement, and also the hardener, should preferably be prepared reproducibly to an accuracy of Δn<0.0002. In order to achieve this accuracy, preferably at least two main constituents, e.g. thiol esters or thiourethanes with different refractive powers are used for the resin component (epoxy compound, component (A)) and/or for the hardener component (thiol ester (B) or oligomeric thiourethane).

The compositions according to the invention have surprisingly proven to be particularly suitable as cements with a high degree of adaptation of the refractive power. It is advantageous to use the above-described oligomers, in particular the oligomeric thiourethanes (reduced volume shrinkage, low stresses on curing, viscosity adapted to the resin component—thereby better miscibility of resin and hardener). Pre-polymeric polythiols can be prepared by complete reaction of polythiols with diisocyanates in deficiency. By carrying out the reaction in a temperature-controlled manner, these pre-polymers can be prepared particularly reproducibly.

The invention further relates to a method for bonding work pieces, comprising the steps that (A) an epoxy compound with two or more epoxy groups, (B) a thiol ester with two or more ester groups and two or more thiol groups, (C) 0.005-2 wt.-%, based on the total weight of the composition, of a tertiary amine which comprises a 5- or 6-membered aliphatic nitrogen heterocycle, and optionally (D) 10-50 wt.-%, based on the total weight of the composition, of an oligomer are mixed and the mixture is then brought into contact with the work pieces to be bonded.

In addition, the invention relates to a method for bonding work pieces, comprising the steps that (A) an epoxy compound with two or more epoxy groups, (B) a thiol ester with two or more ester groups and two or more thiol groups, (C) 0.005-2 wt.-%, based on the total weight of the composition, of a tertiary amine which comprises a 5- or 6-membered aliphatic nitrogen heterocycle, 0.5-2 wt.-% of a photolatent base and a photoinitiator as well as optionally 10-50 wt.-%, based on the total weight of the composition, of an oligomer are mixed, the mixture is brought into contact with the work pieces to be bonded and is then irradiated with light with a wavelength of from 200 to 450 nm, wherein the mixture cures.

Furthermore, a method for producing an optical element which is transparent for a predetermined wavelength range and in which an optically active structure is embedded, is provided which comprises the following steps:
a) providing a first shell which is transparent for the predetermined wavelength range, which is formed in one piece and which comprises on its upper side a structured section,
b) applying a coating which is optically active for the predetermined wavelength range to the structured section in order to form the optically active structure,
c) providing a second shell which is transparent for the predetermined wavelength range, which is formed in one piece and which comprises a smooth underside, which has a complementary shape to the shape of the upper side,
d) applying a composition according to the invention which is transparent for the predetermined wavelength range as adhesive onto the upper side of the first shell and/or the underside of the second shell and
e) joining the upper side of the first shell to the underside of the second shell by means of the adhesive, with the result that a two-shell optical element is produced in which the optically active structure is embedded.

With this method according to the invention, the optical element can be mass-produced with only two shells (in particular with precisely two shells) with the desired accuracy. However, the optical element can also comprise more than two shells as well as two or more parts which are bonded or joined to each other with the composition according to the invention.

In particular, the first and second shells can be provided in the steps a) and c) in each case as dimensionally stable shells. By a dimensionally stable shell is meant in particular a shell which retains its shape when, except for the force of gravity, no other forces are acting on it.

Furthermore, the first and second shells can be provided in the steps a) and c) such that the upper side and the underside are formed curved. In addition, the first and second shells can be provided such that the side facing away from the upper and underside in each case is formed curved. The curvature can be a spherical curvature, an aspherical curvature or another curvature.

The first shell can be provided in step a) such that the upper side is formed as a smooth surface except for the structured section.

In addition, after step b), at least one indentation formed by the structured section can be filled to the upper side with material. The same material is preferably used as the first shell is made from. Furthermore, the composition according to the invention can be used for the filling.

The filling can be carried out in one step or in several filling steps. In particular, the filling is carried out such that there is a smooth, continuous upper side. The filled structured section thus forms a continuous surface together with the rest of the upper side.

In the method according to the invention, in step d), the adhesive can be applied as adhesive layer onto the entire upper side of the first shell and/or the entire underside of the second shell. In particular, the structured section (preferably when it is filled to the upper side with material) can also be provided with the adhesive layer.

The first shell, which can also be referred to as first partial body or first semi-finished part, can be produced from a first polymer material and the second shell, which can also be referred to as second partial body or second semi-finished part, can be produced from a second polymer material. The first polymer material and the second polymer material can, in each case, be a thermoplastic material and/or a thermosetting material. As thermoplastic material e.g., PMMA (polymethyl methacrylate, e.g. Plexiglas), PA (polyamide, e.g. Trogamid CX), COP (cyclo olefin polymers, e.g. Zeonex), PC (polycarbonate, poly(bisphenol A carbonate), e.g. Makrolon, in particular LQ 2647), LSR (Liquid Silicone Rubber, e.g. Silopren, Elastosil), PSU (polysulfone, e.g. Ultrason), PES (polyethersulfone) and/or PAS (poly(arylene sulfone)) can be used. As thermosetting material e.g., ADC (allyl diglycol carbonate, e.g. CR-39), acrylates (e.g. Spectralite), PUR (polyurethanes, e.g. RAVolution), PU/PUR (polyureas, polyurethanes, e.g. Trivex), PTU (polythiourethanes, e.g. MR-8, MR-7) and/or polymers based on episulfide/polythiol (e.g. MR-174) can be used.

In particular, the optically active structure can be completely embedded in the optical element such that it does not extend to an outer boundary surface of the optical element. The optically active structure is preferably smaller in its dimensions than the dimensions of the optical element. It can also be said that the optically active structure is only formed in a part of the optical element. The embedded optically active structure can have a maximum lateral dimension which is smaller than the maximum lateral dimension of the optical element. In particular, it can be smaller than 50% of the lateral dimension of the optical element or also smaller than 40%, 30% or 20% of the lateral dimension of the optical element. The optically active structure is thus preferably provided embedded in the optical element but only in parts.

In the method according to the invention, after step b) and before step d), a protective layer made from thermosetting material can be applied to the optically active coating by pouring. For this, in particular the RIM process (Reaction Injection Moulding process) can be used. Here, e.g. two components can be mixed in a mould immediately before the injection, with the result that the components react with each other and can form a desired chemically crosslinked polymer. The first shell is preferably positioned in a corresponding mould, with the result that the desired protective layer can be formed.

The optically active structure can, for example, be formed as reflective and/or diffractive structure. In particular, the optically active structure can be formed as a partially reflective structure and/or as a wavelength-dependent reflective structure.

The formation of the first and/or second shell can, in particular, in each case be carried out in at least two successive partial steps. This leads to reduced shrinkage during the production of the first or second shell.

In the method according to the invention, those materials can be used as first and second polymer material the refractive indices of which differ by not more than 0.005 or 0.001 for at least one wavelength from the predetermined wavelength range. In particular, the refractive indices may differ by not more than 0.0005. With such a small difference in refractive index, the boundary surface between the two polymer materials disappears almost optically for the predetermined wavelength range. In particular, the polymer materials can be chosen such that they have the same dispersion in the predetermined wavelength range.

The predetermined wavelength range can be the visible wavelength range, the near infrared range, the infrared range and/or the UV range.

In order to provide the first shell according to step a) and the second shell according to step c), in each case a moulding process (such as e.g. injection moulding, injection compression moulding, RIM, casting), a forming process (such as e.g. thermoforming, hot embossing), a removing and/or separating process (such as e.g. diamond cutting, ion bombardment, etching) can be used. Of course, it is also possible to combine these processes for providing the first or second shell with each other.

The first shell and the second shell are in each case in particular formed as a dimensionally stable semi-finished part which are joined to each other by means of the adhesive layer.

In particular, the first shell can have an average thickness from the range of from 2 mm-5 mm (e.g. 3.5 mm) and the second shell can have an average thickness from the range of from 0.15 mm to 2 mm or from the range of from 0.15 mm to 0.25 mm (e.g. 0.17 mm). The ratio of the average thickness of the first shell to the average thickness of the second shell can lie in the range of from 5-40, 10-35, 15-25 or 18-22 (e.g. 20, 20.5 or 21).

The first shell can have an area on the edge (or a marginal area) which has a greater thickness than the average thickness of the first shell. The marginal area is preferably not taken into account in determining the average thickness of the first shell. In addition, the marginal area can be formed in one piece with the first shell or it can be a separate element which is joined to the first shell. For example, the marginal area can be bonded or cemented to the first shell. The marginal area can be formed such that it provides at least one further optical functionality. This can, in particular, be a diffractive and/or reflective optical functionality. In particular, the first shell with the marginal area can be formed such that it is L-shaped.

The application of the optically active coating according to step b) can, for example, take place by vapour coating, sputtering, CVD (chemical vapour deposition), wet coating, etc. The coating can be a single layer. However, it is also possible to apply several layers. In particular, an interference layer system can also be applied. Furthermore, at least one layer for adhesion, one layer for mechanical compensation and a protective layer (diffusion/migration, thermal protection, chemical protection, UV protection etc.) can additionally be applied. The optically active coating can be designed for specific wavelengths or spectral ranges. Furthermore, the function thereof can additionally or alternatively be dependent on the angle of incidence, on the polarization and/or on further optical properties. The optically active structure can be reflective, in particular highly reflective (e.g. mirror-like), partially transparent/partially reflecting and/or can provide a filter effect. Furthermore, the optically active coating can be a diffractive optical element.

The optically active coating may be applied only to the structured section. Alternatively it is possible to apply the optically active coating over the whole surface and then to remove it in the surface sections which are not required. For example, chemical etching or ion etching can be used for such a removal.

At least one metal, at least one metal oxide or at least one metal nitride can be used for the optically active coating. An organic material and/or a polymer material can also be used. Furthermore, so-called hybrid materials, such as e.g. organic-inorganic hybrid systems or organically modified silanes/polysiloxanes can be used.

Furthermore, steps a)-e) can be performed such that the optically active structure comprises surface pieces spaced apart from each other which provide the desired optical function. The surface pieces can, for example, be reflective surface pieces. The reflective surface pieces can bring about a complete reflection (almost 100%) or also only a partial reflection (partially reflective surface pieces). In particular, the reflective surface pieces do not lie in a common plane. They can be offset parallel to each other.

Together, the reflective surface pieces can provide a deflecting effect and, optionally, they can additionally also provide an imaging effect.

The surface pieces can in each case be formed separately as flat surface pieces or also as surface pieces formed curved.

In the method according to the invention, the optical element can be finished after carrying out step e). However, it is also possible to carry out at least one more material-removing processing step in order, for example, to machine or carve out the boundary surface of the second shell facing away from the first shell. The same applies to the boundary surface of the first shell facing away from the second shell.

Of course, at least one more surface-finishing method step can also be carried out, such as e.g. the application of an anti-reflection coating, a hard coating, etc. In particular, the finishing processes known from the manufacture of spectacle lenses can be carried out.

The finished optical element can thus be provided with the method according to the invention. However, it is also possible for yet more method steps to be necessary in order to finish the optical element such that it can be used for its intended use.

Furthermore, an optical element which is transparent for a predetermined wavelength range and in which an optically active structure is embedded, is provided wherein the optical element is produced by the steps of the method according to the invention (including further developments thereof).

In particular, the optical element can be formed as a spectacle lens for a display device that can be fitted on the head of a user and generates an image as well as comprise a front side and a rear side, a coupling-in section and a coupling-out section spaced apart from the coupling-in section and a light guiding channel which guides light bundles of pixels of the generated image, which are coupled into the optical element via the coupling-in section of the optical element, in the optical element to the coupling-out section, by which they are coupled out of the spectacle lens, wherein the coupling-out section comprises the optically active structure, which brings about a deflection of the light bundles for the coupling-out, and wherein the front side is formed by the side of the second shell facing away from the first shell and the rear side is formed by the side of the first shell facing away from the second shell.

Furthermore, an optical element can be provided for a display device that can be fitted on the head of a user and generates an image that comprises a front side and a rear side, a coupling-in section and a coupling-out section spaced apart from the coupling-in section and a light guiding channel which is suitable for guiding light bundles of pixels of the generated image, which are coupled into the optical element via the coupling-in section of the optical element, in the optical element to the coupling-out section, by which they are coupled out of the optical element, wherein the optical element comprises several parts which are joined, preferably bonded, to each other with a composition according to the invention. Furthermore, the optical element is preferably a spectacle lens.

In addition, a display device is provided, with a holder that can be fitted on the head of a user, an image-generating module which generates an image secured to the holder, and an imaging optical system secured to the holder, which comprises an optical element according to the invention and which, when the holder is fitted on the head of the user, images the generated image such that the user can perceive it as a virtual image.

The imaging optical system can comprise the optical element as the only optical element. However, it is also possible for the imaging optical system to also comprise in addition to the optical element at least one further optical element.

The display device can comprise a control unit that actuates the image-generating module.

The image-generating module can in particular comprise a two-dimensional imaging system, such as e.g. an LCD module, an LCoS module, an OLED module or a tilting mirror matrix. The imaging system can comprise a plurality of pixels, which can be arranged e.g. in rows and columns. The imaging system can be self-luminous or not self-luminous.

The image-generating module can, in particular, be formed such that it generates a monochromatic or a multi-coloured image.

The display device according to the invention can comprise further elements known to a person skilled in the art which are necessary for its operation.

Furthermore, a method is provided for the production of the described display device. The optical element according to the invention is produced according to the production method according to the invention and the optical element according to the invention produced in this way is combined (or assembled) with the further elements of the display device such that the display device according to the invention (including further developments thereof) is produced.

It is understood that the features named above and those yet to be explained below can be used not only in the stated combinations but also in other combinations or alone, without departing from the scope of the present invention.

BRIEF DESCRIPTION OF THE DRAWINGS

The invention is explained in even more detail below by way of example with reference to the attached drawings, which also disclose features essential to the invention. For greater clarity, a representation which is accurate in terms of scale and proportion is dispensed with at least partially in the figures and there is no shading. There are shown in.

DETAILED DESCRIPTION OF THE DRAWINGS

Figure 1:
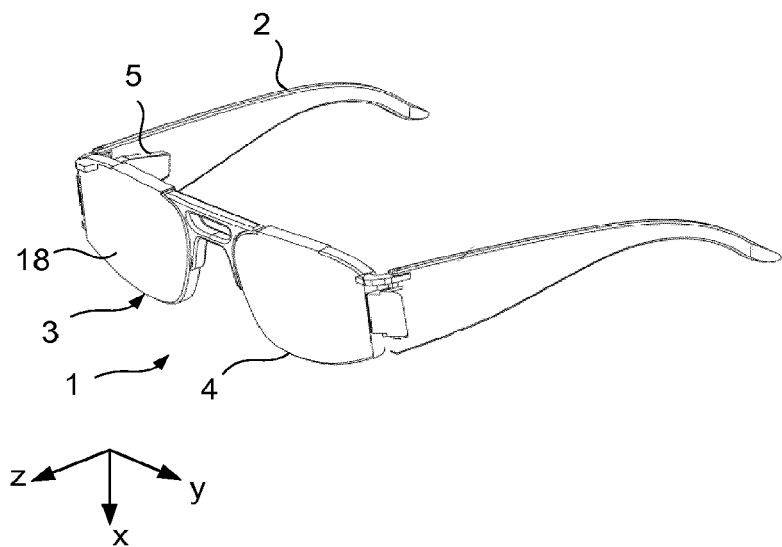
FIG. 1 an embodiment of the display device according to the invention.

In the embodiment shown in FIG. 1, the display device 1 according to the invention comprises a holder 2 that can be fitted on the head of a user, which can be formed e.g. in the manner of a conventional spectacles frame, as well as a first and a second spectacle lens 3, 4, which are secured to the holder 2. The holder 2 with the spectacle lenses 3, 4 can be formed e.g. as sports glasses, sunglasses and/or glasses for correcting defective vision, wherein a virtual image can be reflected into the user's field of view via the first spectacle lens 3, as is described below.

For this purpose, the display device 1 comprises an image-generating module 5, which can be arranged in the area of the right-hand temple stem of the holder 2, as is represented schematically in FIG. 1. The image-generating module 5 can comprise a two-dimensional image-generating element 6 (FIG. 2), such as e.g. an OLED, an LCD or an LCoS chip or a tilting mirror matrix, with a plurality of pixels arranged e.g. in columns and rows.

The spectacle lenses 3 and 4, and in particular the first spectacle lens 3, are only described together with the display device 1 according to the invention by way of example. The spectacle lenses 3, 4, or at least the first spectacle lens 3, are in each case formed separately as a spectacle lens 3, 4 according to the invention or as an optical element according to the invention. The optical element according to the invention can also be used in another context than with the display device 1 described here. Therefore, the optical element, when it is formed as a spectacle lens, can, naturally, also be formed as second spectacle lens 4.

Figure 2:
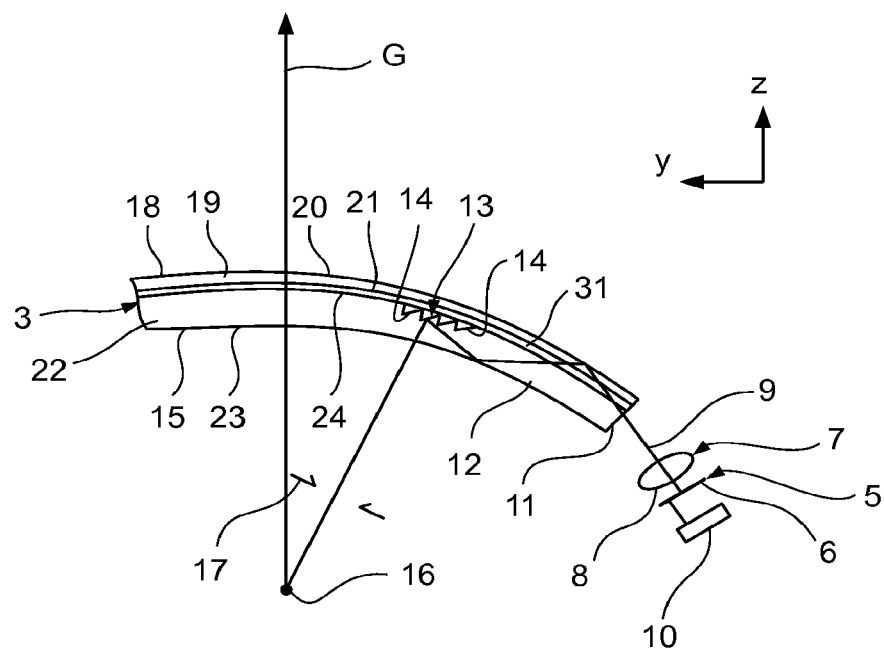
FIG. 2 an enlarged partial sectional view of the optical element 1 according to the invention including a schematic representation of the image-generating module.

As can best be seen from the enlarged schematic partial sectional view in FIG. 2, the display device 1 comprises an imaging optical system 7 which contains an optical element 8 arranged between the image-generating element 6, or the imaging system 6, and the first spectacle lens 3. In addition, the first spectacle lens 3 itself also serves as part of the imaging optical system 7.

A light bundle 9 can emerge from each pixel of the imaging system 6. The desired image can be generated by correspondingly actuating the pixels of the imaging system 6 by means of a control unit 10, which can be part of the image-generating module 5. In FIG. 2, the beam path of a light beam is drawn in to represent the light bundles 9, with the result that the light beam 9 is also discussed hereafter.

The light beam 9 emerging from the imaging system 6 runs through the optical element 8 and enters the first spectacle lens 3 via a coupling-in section 11 (here the end face of the first spectacle lens 3), and is guided in this along a light guiding channel 12 to a coupling-out section 13. The coupling-out section 13 comprises several reflective deflecting surfaces 14 (which can also be referred to as reflective facets) arranged next to each other on which a reflection of the light beams 9 takes place in the direction of a rear side 15 of the first spectacle lens 3, with the result that the light beams 9 exit the first spectacle lens 3 via the rear side 15.

Thus, when a user is wearing the display device 1 according to the invention on his head as intended, he can perceive the image generated by means of the imaging system 6 as a virtual image when he looks at the coupling-out section 13. In the embodiment described here, the user must look towards the right by approx. 40° relative to the direction of view G of a forward view. In FIG. 2, the centre of rotation 16 of the user's eye, as well as the eyebox 17 or the exit pupil 17 of the imaging optical system 7 is drawn in for clarification. The eyebox 17 is the area which is provided by the display device 1 and in which the user's eye can move and he can still see the generated image as a virtual image.

Although in the described embodiment the coupling-in is carried out via the end face of the first spectacle lens 3 and thus the coupling-in section 11 is formed on the end face of the first spectacle lens 3, it is also possible to carry out a coupling-in via the rear side 15 of the first spectacle lens.

As is shown in the schematic representation in FIG. 2, both the rear side 15 and the front side 18 of the first spectacle lens 3 are formed curved.

Furthermore, as can be learned in particular from the representations in FIG. 2, the first spectacle lens 3 is formed with two shells and comprises an outer shell 19 with a first and second side 20 and 21 and an inner shell 22 with a first and second side 23 and 24.

The first side 20 of the outer shell 19 forms the front side 18 of the first spectacle lens 3 and the first side 23 of the inner shell 22 forms the rear side 15 of the first spectacle lens 3. The second side 21 of the outer shell 18 and the second side 24 of the inner shell 22, which face each other, have complementary curvatures and are connected flat to each other via an adhesive layer 31. To form the adhesive layer 31, the composition according to the invention can be used as adhesive for bonding the two shells 19, 22.

The light guiding channel 12 is formed such that the desired guiding of the light beams 9 takes place from the coupling-in section 11 to the coupling-out section 13. This can take place, e.g., through total internal reflection on the front side 18 (=first side 20 of the outer shell 19) and the rear side 15 (=first side 23 of the inner shell 22). Of course, it is also possible for a reflective coating, which brings about the desired reflection of the light beams 9, to be formed on the front side 18 and/or on the rear side 15 in the area of the light guiding channel 12. The reflectivity of the reflective coating can e.g. be as high as possible (approx 100%) or lower. The reflective coating can thus be formed as a mirror layer or as a partially reflective layer.

In the embodiment described here, the two sides 20, 21 of the outer shell 19 are spherically curved and the first side 20 of the outer shell 19 has a radius of curvature of 94 mm and the second side 21 of the outer shell 19 has a radius of curvature of 92 mm. The thickness of the outer shell is thus 2 mm. However, the outer shell 19 can also be formed with a smaller thickness. The thickness of the outer shell 19 can thus be in the range of from 0.15 mm to less than 2 mm. In particular, the outer shell 19 can be formed as a dimensionally stable film. Here, by dimensionally stable is meant in particular that the film at least withstands the force of gravity and thus retains its shape if no other forces are acting on it.

The second side 24 of the inner shell 22 is spherically curved and has a radius of curvature which corresponds to the radius of the second side 21 of the outer shell 19. Here, this is therefore a radius of 92 mm. The first side 23 of the inner shell 22 is spherically curved and has the radius of curvature required to correct the user's defective vision (e.g. 150 mm when PMMA is used as material for the inner shell 22). Of course, the first side 23 of the inner shell can also be aspherically curved. The material of the outer shell 19 is preferably the same as the material of the inner shell 22. The thickness of the inner shell 22 depends substantially on the difference between the radius of the second side 24 of the inner shell 22 and the first side 23 of the inner shell 22 and, in the example described here, is approx. 3 mm.

As already mentioned, the materials of the inner and outer shell 22 and 19 are preferably the same, with the result that they have an identical refractive index. The inner and outer shell 22 and 19 are preferably bonded over the whole surface via the adhesive layer 31, with the result that a compact first spectacle lens 3 is provided.

The first spectacle lens 3 of the embodiment described here provides a correction of +2 dioptres.

Figure 3:
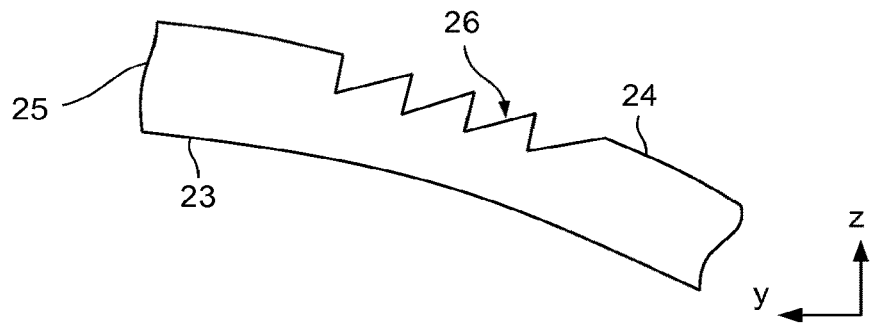
FIGS. 3-7 partial sectional views to explain the production of the optical element according to the invention, and FIG. 8 a partial sectional view to explain an alternative way of producing the optical element according to the invention.

The optical element according to the invention can be produced as follows:

In a first step, a first semi-finished part 25 is produced in the injection mould from a thermoplastic polymer. As is shown in the enlarged partial sectional view from FIG. 3, the first semi-finished part 25 comprises the first side 23 and the second side 24. A microstructuring 26, which simulates the shape of the desired reflective facets 14, is formed on the second side 24.

Figure 4:
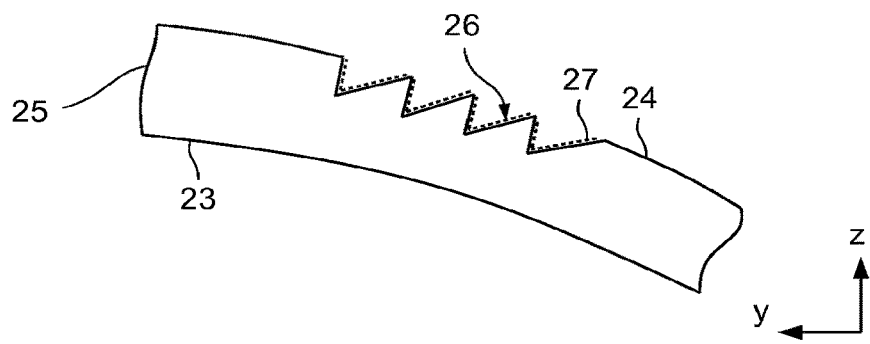

The first semi-finished part 25 is then coated with an optically active layer 27, which is represented with a dotted line, in the area of the microstructuring 26 (to simplify the representation, the layer 27 is not drawn in in FIG. 2). Known coating methods can be used for this, such as e.g. chemical vapour deposition (CVD) or physical vapour deposition (PVD). The optically active layer 27, which is represented with dots in FIG. 4, is chosen such that the described reflective facets 14 are provided.

Figure 5:
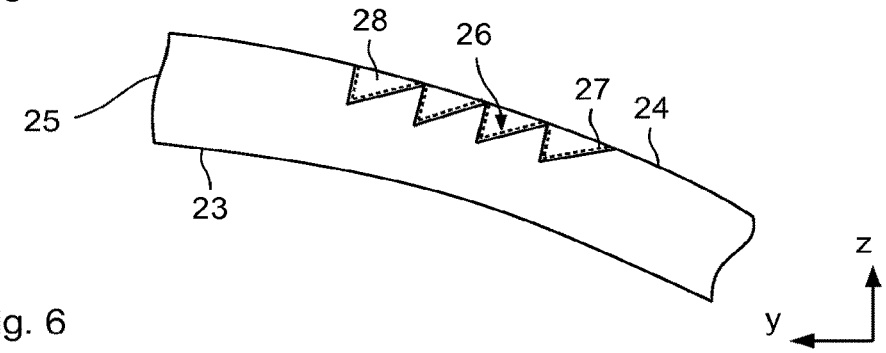

The indentations which are present because of the microstructuring 26, which extend from the second side 24 into the semi-finished part 25, are filled in in a following step such that a smooth continuous second side 24 results (FIG. 5). For filling the indentations, the same material 28 as the material for producing the semi-finished part 25 or an optical cement or optical adhesive 28 can be used. In particular, the composition according to the invention can be used.

Figure 6:
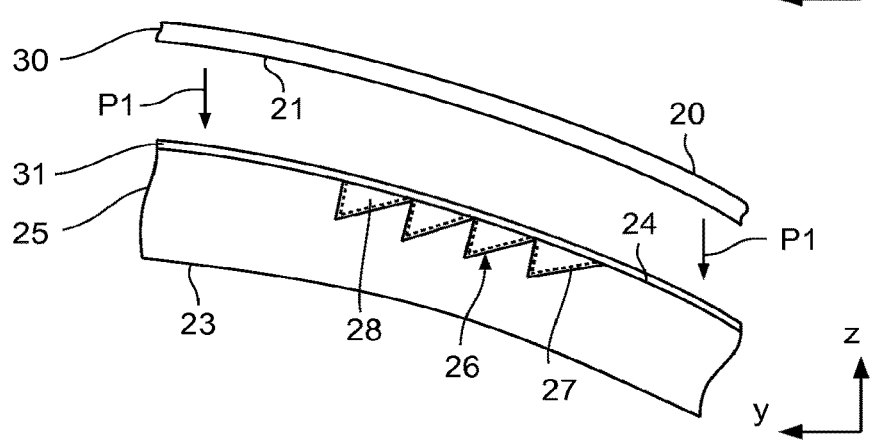
Figure 7:
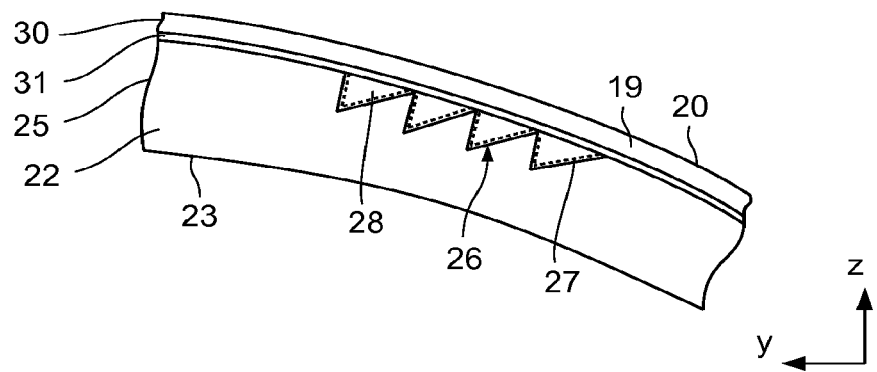

Then, the outer shell 19 is produced in injection moulding from a thermoplastic polymer as second semi-finished part 30 such that it comprises the first and second side 20, 21. Alternatively, the second semi-finished part 30 can be produced before the production of the first semi-finished part 25 or at the same time as the first semi-finished part 25. This second semi-finished part 28 is then bonded to the first semi-finished part 25 over the whole surface. For this, the second side 21 of the second semi-finished part 30 and/or the second side 24 of the first semi-finished part 25 can be coated with an optical adhesive or an optical cement in order to form an adhesive layer 31. In FIG. 6, the case is shown in which the second side 24 of the first semi-finished part 25 is coated with the adhesive layer 31. Then, the two semi-finished parts are brought into contact with each other at their surfaces 21 and 24 via the adhesive layer 31, which can also be referred to as adhesion layer, as is indicated by the arrows P1 in FIG. 6, and the adhesive layer 31 is cured in order thus to produce the optical element 3 according to the invention, as it is shown in FIG. 7. Thus, the optical element 3 according to the invention is present, which is built up in two shells, wherein the outer sides 23 and 20 of the two shells 19 and 22 form the rear side 15 and the front side 18 of the first spectacle lens 3.

Different materials can be used as material for the two semi-finished parts 25 and 30. However, the same material is preferably used for both semi-finished parts 25 and 30. In particular, thermoplastic polymers and/or thermosetting polymers are used.

As thermoplastic polymers e.g., PMMA (polymethyl methacrylate, e.g. Plexiglas), PA (polyamide, e.g. Trogamid CX), COP (cyclo olefin polymers, e.g. Zeonex), PC (polycarbonate, poly(bisphenol A carbonate), e.g. Makrolon), LSR (Liquid Silicone Rubber, e.g. Silopren, Elastosil), PSU (polysulfone, e.g. Ultrason), PES (polyethersulfone) and/or PAS (poly(arylene sulfone)) can be used. As thermosetting polymers e.g., ADC (allyl diglycol carbonate, e.g. CR-39), acrylates (e.g. Spectralite), PUR (polyurethanes, e.g. RAVolution), PU/PUR (polyureas, polyurethanes, e.g. Trivex), PTU (polythiourethanes, e.g. MR-8, MR-7) and/or polymers based on episulfide/polythiol (e.g. MR-174) can be used.

Figure 8:
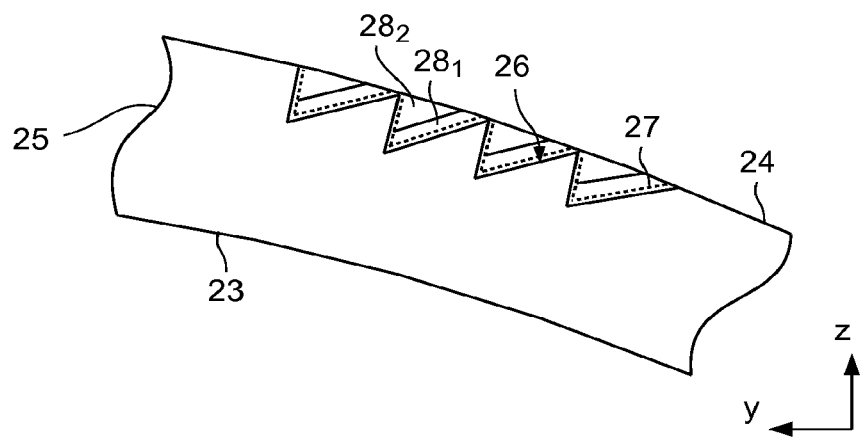

In FIG. 8, in an enlarged sectional representation, the first semi-finished part 25 is shown with the microstructuring 26 and the optically active layer 27. Unlike in the previously described filling in of the microstructuring 26 in one step, in the variant according to FIG. 8 this is carried out in two steps. In this way, an undesired shrinkage which can occur on curing of the material of the filling layers $28_1$, $28_2$ (filling layer $28_1$ and then filling layer $28_2$) can be minimized. Of course, the filling in can also be carried out in more than two steps, e.g. in three, four, five or six steps.

In the display device 1 according to the invention the virtual image is reflected into the user's field of view via the first spectacle lens 3. Of course, a reflection via the second spectacle lens 4 is also possible. Furthermore, the display device 1 can be formed such that items of information or virtual images can be reflected via both spectacle lenses 3, 4. The reflection can take place such that a three-dimensional image impression results. However, this is not absolutely necessary.

The spectacle lenses 3, 4 can have a refractive power of zero or a refractive power different from zero (in particular for the correction of defective vision). As is shown in the figures, both the front side 11 and the rear side 12 of the spectacle lens 3 are formed curved. In particular, the front side 11 can be spherically curved. If the spectacle lens has a refractive power different from zero, in order to correct defective vision, as a rule the curvature of the rear side 15 is chosen appropriately, in order to achieve the corresponding correction. The rear side 15 can have a curvature which differs from the spherical shape.

The holder 2 does not have to be formed as a spectacle-type holder. Any other type of holder with which the display device can be fitted or worn on the head of the user is also possible.

In the described embodiment examples, the spectacle lens 3 is formed with two shells. However, it is also possible to produce the spectacle lens with more than two shells, e.g. at least three shells. In particular, the spectacle lens can be produced from two parts (which do not necessarily need to be shells) or from more than two parts. The shells or parts are then preferably bonded with the composition according to the invention.

The Following Examples Explain the Invention.

The compositions mentioned below were prepared by mixing the components in the stated sequence of the resin and by producing the hardener separately therefrom by mixing the components in the named sequence of the hardener and by subsequently mixing resin and hardener in the stated ratio. Where stated, the mixing of resin and hardener took place in dual cartridges, as are customary in adhesive technology, in which resin and hardener are mixed by pushing them through a mixing section in the form of a helix (static mixing tube), wherein the ratio x+y, for example 2+1, indicates the weight ratio of resin to hardener.

With the adhesives described below, sufficiently long processing times of about 60-120 min. could be obtained accompanied by a complete full cure within about 4-6 hours (at room temperature) and excellent adhesion was achieved. With the described embedding media, excellent image qualities could be obtained on the microscopic examination of tissue sections.

1. Adhesives: Structural Adhesives, Setting Adhesives

EXAMPLE 1

Resin: 100 parts by weight Araldite F
   3 parts by weight Glymo
   0.02 parts by weight Seripas Red
Hardener: 100 parts by weight pre-polymer PTMP/XDI (100+10 parts by weight)
   3 parts by weight 1-(2-hydroxyethyl)pyrrolidine as amine base
Batch: 100 parts by weight resin+80 parts by weight hardener

EXAMPLE 2

Resin: 75 parts by weight Araldite F
   20 parts by weight colourless resin adhesive 52A (plasticized epoxy resin)
   5 parts by weight glycerol tribenzoate
   3 parts by weight Glymo
   0.02 parts by weight Seripas Red
Hardener: 40 parts by weight pre-polymer PTMP/XDI (100+10 parts by weight)
   60 parts by weight PTMP
   5 parts by weight 1-ethylpiperazine as amine base
Suitable for application in 2+1 dual cartridges

EXAMPLE 3

Resin: 50 parts by weight Araldite F
  50 parts by weight Nanopox F 440
  3 parts by weight glycerol tribenzoate
  3 parts by weight Glymo
  0.02 parts by weight Seripas Red
Hardener: 100 parts by weight PTMP
  0.35 parts by weight DABCO as amine base
Suitable for application in 2+1 dual cartridges

EXAMPLE 4

Resin: 100 parts by weight Araldite F
  3 parts by weight Glymo
  0.02 parts by weight Sudan Blue
  50 parts by weight Silbond FW 12 EST (fused silica flour, silanized)
Hardener: 100 parts by weight pre-polymer PTMP/XDI (100+10 parts by weight)
  0.5 parts by weight DABCO as amine base
Batch: 100 parts by weight resin+55 parts by weight hardener

EXAMPLE 5

Resin: 100 parts by weight Epalloy 5000
  3 parts by weight Glymo
  0.02 parts by weight Sudan Blue
Hardener: 100 parts by weight PTMP
  0.5 parts by weight DABCO as amine base
Suitable for application in 2+1 dual cartridges

EXAMPLE 6

Resin: 30 parts by weight Rutapox 0158
  30 parts by weight Rutapox 0162
  40 parts by weight 1,4-butanediol diglycidyl ether
  3 parts by weight Glymo
  0.02 parts by weight Sudan Blue
Hardener: 100 parts by weight pre-polymer PTMP/XDI (100+10 parts by weight)
  0.1 parts by weight DBU as amine base
Suitable for application in 1+1 dual cartridges

EXAMPLE 7

Resin: 50 parts by weight Rutapox 0158
  50 parts by weight Rutapox 0162
  3 parts by weight Glymo
  0.02 parts by weight Sudan Blue
Hardener: 70 parts by weight pre-polymer PTMP/XDI (100+10 parts by weight)
  30 parts by weight Thioplast G44
  0.25 parts by weight DABCO as amine base
Suitable for application in 1+1 dual cartridges

EXAMPLE 8

Resin: 20 parts by weight Araldite F
  60 parts by weight Nanopox F 440
  20 parts by weight IPDX CL 16
  0.02 parts by weight Sudan Blue
Hardener: 100 parts by weight PTMP
  4 parts by weight MTMO (3-mercaptopropyltrimethoxysilane)
  0.3 parts by weight DABCO as amine base
Suitable for application in 2+1 dual cartridges 2. Adhesives with Optical Properties: Cements, Embedding Media for Microscopy

EXAMPLE 9

Resin: 60 parts by weight Rutapox 0158
  40 parts by weight Rutapox 0162
  2 parts by weight Glymo, distilled
Hardener: 100 parts by weight PTMP
  0.12 parts by weight DABCO as amine base
Batch: 100 parts by weight resin+70 parts by weight hardener
Refractive power (cured) at 20° C.: ne=1.596

EXAMPLE 10

Resin: 35 parts by weight Rutapox 0158
  25 parts by weight Rutapox 0162
  40 parts by weight 1,4-butanediol diglycidyl ether, distilled
  2 parts by weight Glymo, distilled
Hardener: 100 parts by weight PTMP
  0.25 parts by weight DABCO (amine base)
Batch: 100 parts by weight resin+85 parts by weight hardener
Refractive power (cured) at 20° C.: ne=1.571

EXAMPLE 11

Resin: 40 parts by weight Epalloy 5000, distilled
  60 parts by weight Erisys GE 22, distilled
  3 parts by weight Glymo, distilled
Hardener: 100 parts by weight pre-polymer TPMP/XDI (100+5.6 parts by weight)
  4 parts by weight 1-(2-hydroxyethyl)piperazine, distilled as amine base
Batch: 100 parts by weight resin+90 parts by weight hardener
Refractive power (cured) at 20° C.: ne=1.540

EXAMPLE 12

Resin: 60 parts by weight Rutapox 0158
  40 parts by weight Rutapox 0162
  2 parts by weight Glymo, distilled
Hardener: 50 parts by weight PTMP
  50 parts by weight TEMPIC
  0.2 parts by weight DABCO as amine base
Batch: 100 parts by weight resin+85 parts by weight hardener
Refractive power (cured) at 20° C.: ne=1.592

EXAMPLE 13

Resin: 62 parts by weight Rutapox 0158
  38 parts by weight Rutapox 0162
  2 parts by weight Glymo, distilled
Hardener: 100 parts by weight MR7 B
  0.12 parts by weight DABCO as amine base
Batch: 100 parts by weight resin+50 parts by weight hardener
Refractive power (cured) at 20° C.: ne=1.637

3. UV Activatable Adhesive Systems:
The UV activation takes place by irradiating with a high-pressure mercury vapour lamp or with a UV LED preferably at 365 nm. Irradiation rate approx. 80-120 mW/cm² for 30 to 120 seconds. During the UV activation there is a rapid colour change of the mixed adhesive from blue to yellow (colour indicator for the UV activation).

EXAMPLE 14

Resin: 100 parts by weight Araldite F
  3 parts by weight Glymo
  5 parts by weight Darocur 1173 (radical initiator)
  0.02 parts by weight Sudan Blue
Hardener: 100 parts by weight pre-polymer PTMP/XDI (100+10 parts by weight)
  5 parts by weight methoxycarbonylbenzyl DBN as photolatent amine base
  2 parts by weight 1-ethylpiperazine as additional amine base
Batch: 100 parts by weight resin+80 parts by weight hardener

EXAMPLE 15

Resin: 40 parts by weight Araldite F
  60 parts by weight Nanopox F 440
  3 parts by weight Glymo
  6 parts by weight Darocur 1173 (radical initiator)
  0.02 parts by weight Sudan Blue
Hardener: 80 parts by weight PTMP
  20 parts by weight TEMPIC
  5 parts by weight methoxycarbonylbenzyl DBN as photolatent amine base
Suitable for application in 2+1 dual cartridges

EXAMPLE 16

Resin: 30 parts by weight Epalloy 8330*
  70 parts by weight Araldite F
  8 parts by weight Darocur 1173
  5 parts by weight Glymo
  0.02 parts by weight Sudan Blue
  35 parts by weight Silbond FW 12 EST
  30 parts by weight Silbond FW 600 EST
*epoxidized phenol novolac resin, manufacturer CVC Specialty Chemicals
Hardener: 100 parts by weight pre-polymer PTMP/XDI (100+12 parts by weight)
  5 parts by weight PL-DBN**
  0.1 parts by weight DABCO (amine catalyst)
** PL-DBN=photolatent amine base DBN
photoactivatable, suitable for 2+1 dual cartridges
4. Cement with High Adaptation of Refractive Power to Polycarbonate:

EXAMPLE 17

Resin: 90 parts by weight Araldite F
  10 parts by weight Epalloy 5000
  3 parts by weight Glymo
  $n_e^{21}=1.5649$, $D_{20}=1.175$ g/cm$^3$
Hardener: 90 parts by weight pre-polymer PTMP/XDI (100+10 parts by weight)
  10 parts by weight pre-polymer MR7 B/XDI (100+20 parts by weight)
  0.1 parts by weight DABCO (amine catalyst)
  $n_e^{21}=1.5568$, $D_{20}=1.300$ g/cm$^3$
Batch: 100 parts by volume resin
  60 parts by volume hardener (processing with mixing equipment)
  mixture $n_e^{21}=1.5609$
  pot life (2 g) approx. 60 min.
cured $n_e^{21}=1.5912$
polycarbonate (LQ 2647) $n_e^{21}=1.5912$
target wavelength is 546 nm ($n_e$)
Measured Values of the Cured Mixture According to Example 16:
  $n_g$ (435.8 nm)=1.6078
  $n_{F'}$ (480.0 nm)=1.5996
  n (508.5 nm)=1.5955
  $n_e$ (546.1 nm)=1.5910, after a further 5 d/RT 1.5912 (thereafter refractive power stable)
  n (578.0 nm)=1.5880
  $n_g$ (589.3 nm)=1.5870
  $n_c$ (643.8 nm)=1.5826
    $(n_{F'}-n_c^1)=0.0170$
    $\vartheta_e=34.8$
Comparison with Makrolon (Polycarbonate; LQ 2647), flat plate D=80 mm, d=2 mm
  $n_g$ (435.8 nm)=1.6123
  $n_{F'}$ (480.0 nm)=1.6017
  n (508.5 nm)=1.5966
  $n_e$ (546.1 nm)=1.5912
  n (578.0 nm)=1.5875
  $n_D$ (589.3 nm)=1.5864
  $n_c$ (643.8 nm)=1.5819
    $(n_{F'}-n_c^1)=0.0198$
    $\vartheta_e=29.9$ The cements can additionally also contain additives, e.g. against yellowing through the action of daylight/sunlight in the form of so-called UV absorbers, e.g. Tinuvin P, Tinuvin 109, Tinuvin 900 or 2,4-dihydroxybenzophenone.

Described above are just a few exemplary embodiments of the present invention. The principle according to the present invention is naturally subject to modifications within the scope of protection defined by the claims, regarding for example implementation details as well as fields of use. The present invention is not limited solely to the foregoing exemplary embodiment, but many variations are possible while remaining within an inventive concept defined by the claims.

The invention claimed is:

1. A composition comprising:
  (A) an epoxy compound with two or more epoxy groups,
  (B) at least one oligomeric thiourethane, and
  (C) a tertiary amine comprising a 5- or 6-membered aliphatic nitrogen heterocycle in an amount of 0.005-2 wt.-%, based on the total weight of the composition,
  wherein the composition contains less than 1 wt.-%, based on the total weight of the composition, of a primary amine; and
  wherein an average number of monomers comprising the oligomeric thiourethane is between 3 and 100.

2. The composition of claim 1, wherein the tertiary amine is selected from the group consisting of 1-(2-hydroxyethyl)pyrrolidine, 1-(2-hydroxyethyl)pyrrolidone, 1-(2-hydroxyethyl)piperidine, 1-ethylpiperazine, 1-(2-hydroxyethyl)piperazine, 1,4-bis-(2-hydroxyethyl)piperazine, 1-methylimidazole, 4-(2-hydroxyethyl)morpholine, 1,4-diazabicyclo[2.2.2]octane (DABCO), 1,5-diazabicyclo[4.3.0]non-5-ene (DBN), and 1,8-diazabicyclo[5.4.0]undec-7-ene (DBU).

3. The composition of claim 1, wherein the oligomeric thiourethane comprises at least 4 free thiol groups.

4. The composition of claim 1, wherein an average number of monomers comprising the oligomeric thiourethane is between 5 and 25.

5. The composition of claim 1, comprising two or more oligomeric thiourethanes.

6. The composition of claim 4, wherein an average number of the monomers contained in the oligomeric thiourethane is between 5-25 and a proportion of the oligomeric thiourethane or of the oligomeric thiourethanes, based on the total weight of the composition, is 10-50 wt.-%.

7. The composition of claim 1, wherein the at least one oligomeric thiourethane is made from pentaerythritol tetra (3-mercaptopropionate) (PTMP) with xylylene diisocyanate (XDI), pentaerythritol tetra(3-mercaptopropionate) with norbornyl diisocyanate (NBDI), or pentaerythritol tetra(3-mercaptopropionate) with isophorone diisocyanate (IPDI).

8. The composition of claim 1, wherein
(A) the epoxy compound with two or more epoxy groups comprises bisphenol A diglycidyl ether and/or bisphenol F diglycidyl ether,
(B) the at least one oligomeric thiourethane is present in an amount of 10-50 wt.-% is obtained from pentaerythritol tetra(3-mercaptopropionate) (PTMP) and/or trimethylolpropane tri(3-mercaptopropionate) (TPMP) with xylylene diisocyanate (XDI), norbornyl diisocyanate (NBDI) and/or isophorone diisocyanate (IPDI), wherein each oligomeric thiourethane comprises two or more free thiol groups, and
(C) the tertiary amine comprising the 5- or 6-membered aliphatic nitrogen heterocycle is selected from the group consisting of 1,5-diazabicyclo[4.3.0]non-5-ene (DBN), 1,8-diazabicyclo[5.4.0]undec-7-ene (DBU) and 1,4-diazabicyclo[2.2.2]octane (DABCO) in an amount of 0.005-0.3 wt.-%, based on the total weight of the composition, or 1-(2-hydroxyethyl)pyrrolidine, 1-(2-hydroxyethyl)pyrrolidone, 1-(2-hydroxyethyl)piperidine, 1-ethylpiperazine, 1-(2-hydroxyethyl)piperazine, 1,4-bis-(2-hydroxyethyl)piperazine, 1-methylimidazole and 4-(2-hydroxyethyl)morpholine, in an amount of 0.3-2 wt.-%, based on the total weight of the composition.

9. The composition of claim 1, wherein the composition further comprises
(D) a photolatent base in an amount of 0.5-2 wt.-% selected from the group consisting of substituted 5-(carbonylarylmethyl)-1,5-diazabicyclo[4.3.0]nonane and substituted 8-(carbonylarylmethyl)-1,8-diazabicyclo[5.4.0]undecane, and
(E) a photoinitiator.

10. An adhesive comprising the composition according to claim 1.

11. A cement comprising the adhesive according to claim 10.

12. An embedding medium for microscopy comprising the composition according to claim 1.

13. An optical element for a display device that can be fitted on the head of a user and generates an image, the optical element comprising
a front side and a rear side,
a coupling-in section and a coupling-out section spaced apart from the coupling-in section, and
a light guiding channel which is suitable for guiding light bundles of pixels of the generated image, which are coupled into the optical element via the coupling-in section of the optical element, in the optical element to the coupling-out section, by which they are coupled out of the optical element,
wherein the optical element comprises an inner and an outer shell joined to each other with a composition according to claim 1.

14. A display device having a holder that can be fitted on the head of a user, an image-generating module secured to the holder, which generates an image, and an imaging optical system secured to the holder, which comprises an optical element according to claim 13 and which, when the holder is fitted on the user's head, images the generated image such that the user can perceive it as a virtual image.

15. The composition of claim 4, wherein the oligomeric thiourethane is obtained by reacting at least one thiol ester that comprises two or more ester groups and two or more thiol groups and/or at least one thioether that comprises two or more thiol groups, with at least one di- or polyisocyanate, wherein the oligomeric thiourethane comprises two or more free thiol groups.

16. The composition of claim 5, wherein the oligomeric thiourethanes is obtained by reacting at least one thiol ester that comprises two or more ester groups and two or more thiol groups and/or a thioether that comprises two or more thiol groups, with at least one di- or polyisocyanate, wherein each oligomeric thiourethane comprises two or more free thiol groups.

17. The composition of claim 5, wherein an average number of the monomers contained in the oligomeric thiourethane is between 5-25 and a proportion of the oligomeric thiourethane or of the oligomeric thiourethanes, based on the total weight of the composition, is 10-50 wt.-%.

18. The composition of claim 1, wherein the at least one oligomeric thiourethane is a thioether comprising 2,3-bis(2-mercaptoethylsulfanyl)propane-1-thiol.

* * * * *